United States Patent
On

(10) Patent No.: US 10,405,736 B2
(45) Date of Patent: Sep. 10, 2019

(54) CAPSULE ENDOSCOPE, ENDOSCOPE SYSTEM, AND METHOD FOR OPERATING CAPSULE ENDOSCOPE

(71) Applicant: OLYMPUS CORPORATION, Hachioji-shi, Tokyo (JP)

(72) Inventor: Seigo On, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 317 days.

(21) Appl. No.: 15/391,793

(22) Filed: Dec. 27, 2016

(65) Prior Publication Data

US 2017/0105610 A1 Apr. 20, 2017

Related U.S. Application Data

(63) Continuation of application No. PCT/JP2015/062777, filed on Apr. 28, 2015.

(30) Foreign Application Priority Data

Jul. 16, 2014 (JP) .................. 2014-145606

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00006* (2013.01); *A61B 1/00009* (2013.01);
(Continued)

(58) Field of Classification Search
CPC ..... A61B 1/041; A61B 1/045; A61B 1/00016; A61B 1/00009; A61B 1/00006
See application file for complete search history.

(56) References Cited

U.S. PATENT DOCUMENTS 6,709,387 B1 3/2004 Glukhovsky et al.
8,159,549 B2 * 4/2012 Glukhovsky ...... A61B 1/00009
348/22

(Continued)

FOREIGN PATENT DOCUMENTS

JP 2004521662 A 7/2004
JP 2006223892 A 8/2006
(Continued)

OTHER PUBLICATIONS

International Search Report (ISR) and Written Opinion dated Jul. 21, 2015 issued in International Application No. PCT/JP2015/062777.

*Primary Examiner* — John P Leubecker
*Assistant Examiner* — Shankar Raj Ghimire
(74) *Attorney, Agent, or Firm* — Holtz, Holtz & Volek PC

(57) ABSTRACT

A capsule endoscope includes an imaging device that captures time-series captured images and a processor including hardware. The processor implements a process that performs a first motion determination process with respect to the capsule endoscope based on the captured images to calculate a first motion determination result, and a communication process that transmits the captured images to an external device that is provided outside the capsule endoscope, and receives a second motion determination result, the second motion determination result being a result of a second motion determination process with respect to the capsule endoscope that was performed by the external device based on the captured images. The processor implements the process that controls the frame rate of the imaging device based on the first motion determination result and the second motion determination result.

12 Claims, 20 Drawing Sheets

(51) Int. Cl.
*A61B 1/045* (2006.01)
*G02B 23/24* (2006.01)
(52) U.S. Cl.
CPC .......... *A61B 1/00016* (2013.01); *A61B 1/045* (2013.01); *G02B 23/2476* (2013.01)

(56) References Cited

U.S. PATENT DOCUMENTS

| | | | | |
|---|---|---|---|---|
| 2007/0098379 | A1* | 5/2007 | Wang | A61B 1/00009 396/14 |
| 2008/0051642 | A1* | 2/2008 | Krupnik | A61B 1/00009 600/302 |
| 2009/0149704 | A1* | 6/2009 | Mitsuhashi | A61B 1/00009 600/109 |
| 2009/0322865 | A1* | 12/2009 | Wang | A61B 1/00009 348/68 |
| 2010/0130818 | A1* | 5/2010 | Jung | A61B 1/00006 600/109 |
| 2012/0271104 | A1* | 10/2012 | Khait | A61B 1/041 600/109 |
| 2013/0109915 | A1* | 5/2013 | Krupnik | G06T 3/4038 600/109 |
| 2014/0272765 | A1* | 9/2014 | Andreiko | A61B 1/00006 433/27 |
| 2016/0217591 | A1* | 7/2016 | Krupnik | G06T 7/60 |

FOREIGN PATENT DOCUMENTS

| | | | |
|---|---|---|---|
| JP | 2009195271 | A | 9/2009 |
| JP | 2010035746 | A | 2/2010 |
| JP | 2010524557 | A | 7/2010 |

\* cited by examiner

CAPSULE ENDOSCOPE, ENDOSCOPE SYSTEM, AND METHOD FOR OPERATING CAPSULE ENDOSCOPE

CROSS REFERENCE TO RELATED APPLICATION

This application is a continuation of International Patent Application No. PCT/JP2015/062777, having an international filing date of Apr. 28, 2015, which designated the United States, the entirety of which is incorporated herein by reference. Japanese Patent Application No. 2014-145606 filed on Jul. 16, 2014 is also incorporated herein by reference in its entirety.

BACKGROUND

The present invention relates to a capsule endoscope, an endoscope system, a method for operating a capsule endoscope, and the like.

A capsule endoscope is small, and is normally controlled with respect to the frame rate in order to reduce the number of captured images so as to reduce power consumption, for example. The frame rate of the capsule endoscope is controlled corresponding to the speed at which the capsule endoscope moves through the digestive tract. The frame rate of the capsule endoscope is decreased when the motion speed is low, and is increased when the motion speed is high.

For example, JP-A-2006-223892 discloses a frame rate control method. According to the method disclosed in JP-A-2006-223892, a capsule main body that has been introduced into the body of a subject through swallowing captures images using a camera, and transmits the captured images to a reception device (extracorporeal device) that is situated outside the body of the subject. A processor device (extracorporeal device) that is situated outside the body of the subject detects the motion amount (analyzes the motion of the capsule main body) from the degree of similarity between the received captured images, determines an appropriate frame rate based on the motion amount, and transmits information about the frame rate to the capsule main body to control the frame rate of the camera provided to the capsule main body.

JP-A-2010-35746 discloses another frame rate control method. According to the method disclosed in JP-A-2010-35746, a capsule main body that has been introduced into the body of a subject through swallowing captures images using a camera, and transmits the captured images to a reception device (extracorporeal device) that is situated outside the body of the subject. A processor device (extracorporeal device) that is situated outside the body of the subject acquires information about the peristalsis of the digestive tract (organ) using a sound sensor, determines the degree of similarity between the received captured images, measures the motion of the capsule main body from the information about the peristalsis and the determination result for the degree of similarity, sets the frame rate to a normal frame rate or a special frame rate based on the measurement results, and transmits information about the frame rate to the capsule main body to control the frame rate of the camera provided to the capsule main body.

SUMMARY

According to one aspect of the invention, there is provided a capsule endoscope comprising:

an imaging device that captures time-series captured images;

a processor comprising hardware, the processor being configured to implement;

a process that performs a first motion determination process with respect to the capsule endoscope based on the captured images to calculate a first motion determination result; and a communication process that transmits the captured images to an external device that is provided outside the capsule endoscope, and receives a second motion determination result, the second motion determination result being a result of a second motion determination process with respect to the capsule endoscope that was performed by the external device based on the captured images, wherein the processor is configured to implement the process that controls a frame rate of the imaging device based on the first motion determination result and the second motion determination result.

According to another aspect of the invention, there is provided an endoscope system comprising:

a capsule endoscope; and an external device, the capsule endoscope comprising:

an imaging device that captures captured images in time series;

a processor comprising hardware, the processor being configured to implement;

a first process that performs a first motion determination process with respect to the capsule endoscope based on the captured images, and outputs a first motion determination result; and a first communication process that transmits the captured images to the external device, and the external device comprising:

a second process that performs a second motion determination process with respect to the capsule endoscope based on the captured images, and outputs a second motion determination result; and a second communication process that transmits the second motion determination result to the first communication section, wherein the processor is configured to implement the first process that controls a frame rate of the imaging device based on the first motion determination result and the second motion determination result.

According to another aspect of the invention, there is provided a method for operating a capsule endoscope comprising:

capturing time-series captured images;

performing a first motion determination process with respect to the capsule endoscope based on the captured images to calculate a first motion determination result;

transmitting the captured images to an external device that is provided outside the capsule endoscope;

receiving a second motion determination result, the second motion determination result being a result of a second motion determination process with respect to the capsule endoscope that was performed by the external device based on the captured images; and controlling a frame rate used when capturing the captured images based on the first motion determination result and the second motion determination result.

DESCRIPTION OF EXEMPLARY EMBODIMENTS

The exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. Outline

It is impossible to provide a processor having high processing capacity (high-performance processor) to a capsule endoscope that has a small size, and it is difficult to cause the capsule endoscope to perform a high-load process (e.g., motion determination process). Therefore, the frame rate of the capsule endoscope has been controlled through a motion determination process that is performed by an external device that is provided outside the body. The frame rate of the capsule endoscope is controlled corresponding to the speed (physical motion) at which the capsule endoscope advances through the digestive tract. For example, the frame rate of the capsule endoscope is increased when the motion speed of the capsule endoscope has increased.

However, since it is necessary to transmit an image (i.e., large-volume data) from the capsule endoscope to the external device, a time lag may occur until the frame rate is changed after the motion speed of the capsule endoscope has changed. For example, if it takes time to increase the frame rate after the motion speed of the capsule endoscope has increased, the capsule endoscope advances at high speed through the digestive tract in a state in which the frame rate is low, and part of the object may not be captured within the images. In such a case, the doctor may miss a lesion when making a diagnosis, or it may be difficult for the doctor to make a correct diagnosis.

Figure 1:
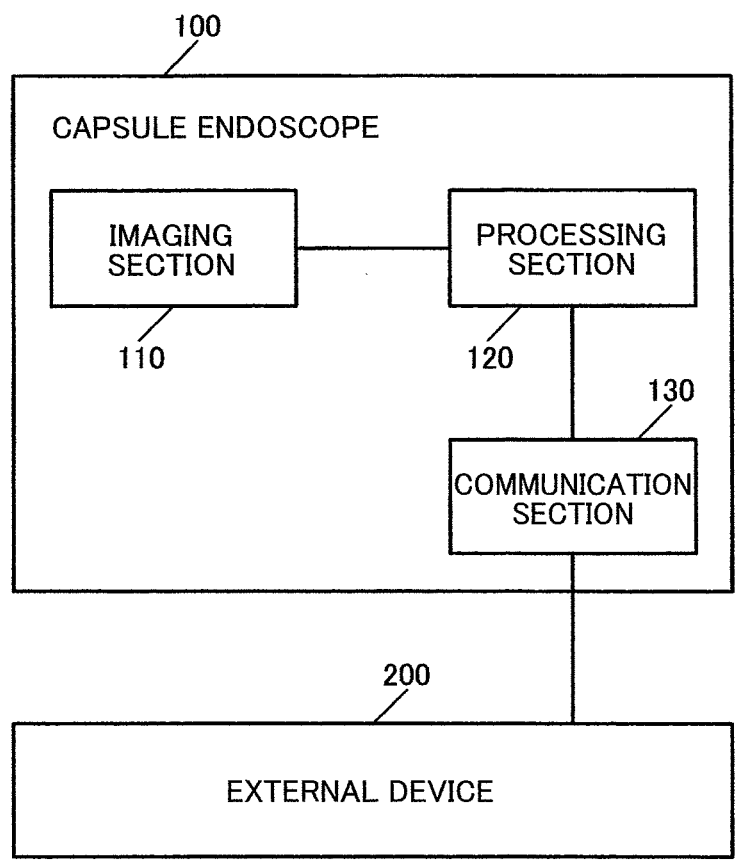
FIG. 1 illustrates a configuration example of an endoscope system.

FIG. 1 illustrates a configuration example of an endoscope system according to the embodiments of the invention that can solve the above problem. The endoscope system includes a capsule endoscope 100 and an external device 200. The capsule endoscope 100 includes an imaging section 110, a processing section 120, and a communication section 130.

The imaging section 110 (imaging device) captures time-series captured images. The processing section 120 performs a first motion determination process with respect to the imaging section 110 based on the captured images to calculate a first motion determination result. The communication section 130 transmits the captured images to the external device 200 that is provided outside the capsule endoscope 100. The external device 200 performs a second motion determination process with respect to the imaging section 110 based on the captured images transmitted from the communication section 130, and the communication section 130 receives the result of the second motion determination process (second motion determination result) from the external device 200. The processing section 120 controls the frame rate of the imaging section 110 based on the first motion determination result and the second motion determination result.

The term "time-series captured images" used herein refers to images that were captured while the capsule endoscope 100 passes through the digestive tract, and are arranged in order of the capture time. For example, the time-series captured images may be a video, or may be a series of images captured at given time intervals. The term "frame rate" used herein refers to the number of images to be captured by the imaging section 110 per unit time. The frame rate may be a capture cycle or time interval.

According to the above configuration, it is possible to cause the capsule endoscope 100 that is limited in terms of hardware scale to perform the first motion determination process in a simplified manner, and adaptively control the frame rate. Since the first motion determination process is performed by the capsule endoscope 100, it is possible to control the frame rate so that a time lag does not occur with respect to a change in the motion speed of the capsule endoscope 100, and reduce or suppress the occurrence of an incorrect diagnosis and the like. Since the second motion determination process with high accuracy can be performed by the external device 200, it is possible to cause the frame rate to accurately follow the motion speed of the capsule endoscope 100.

According to the embodiments of the invention, the processing section 120 performs a first determination process that determines the frame rate based on the first motion determination result, and controls the frame rate based on the first determination process. The processing section 120 performs a second determination process that determines whether or not the frame rate determined based on the first motion determination result is appropriate based on the second motion determination result, and controls the frame rate by determining the frame rate based on the second motion determination result when the processing section 120 has determined that the frame rate determined based on the first motion determination result is not appropriate.

For example, the processing section 120 performs the first motion determination process in the step S112 illustrated in FIG. 9, determines the frame rate based on the determination value of the first motion determination process in the step S113, and switches the frame rate in the step S114 (as described later). The processing section 120 performs the second motion determination process in the step S116, and determines whether or not the frame rate set based on the first motion determination process is appropriate in the step S118. When it has been determined that the frame rate is not appropriate, the processing section 120 determines the frame rate based on the determination value of the second motion determination process, and switches the frame rate in the step S119.

According to this configuration, it is possible to determine the appropriateness of the result of the first motion determination process that was performed by the capsule endoscope 100 in a simplified manner, using the accurate second motion determination process that was performed by the external device 200, and appropriately correct the result of the first motion determination process. Specifically, it is possible to promptly switch the frame rate corresponding to a change in the motion of the capsule endoscope 100 through the first motion determination process, and accurately control the frame rate by causing the external device 200 that is relatively less limited in terms of hardware scale to perform the accurate second motion determination process.

According to the embodiments of the invention, the processing section 120 determines whether or not to switch the frame rate to a frame rate that is higher than the current frame rate based on the first motion determination result, and determines whether or not to switch the frame rate to a frame rate that is lower than the current frame rate based on the second motion determination result.

For example, the processing section 120 determines whether or not to switch the frame rate from the low-speed frame rate to the high-speed frame rate based on the determination value of the first motion determination process in the step S182 illustrated in FIG. 13 (flowchart) (as described later). The frame rate is not switched when the current frame rate is the high-speed frame rate (see steps S181 and S184). The processing section 120 determines whether or not to switch the frame rate from the high-speed frame rate to the low-speed frame rate based on the determination value of the second motion determination process in the step S203 illustrated in FIG. 14 (flowchart). The frame rate is not switched when the current frame rate is the low-speed frame rate (see steps S201 and S202).

Since the capsule endoscope 100 performs the first motion determination process in a simplified manner (see above), the determination accuracy of the first motion determination process is relatively lower than that of the second motion determination process that is performed by the external device 200. Therefore, if the frame rate is switched to a low frame rate based on the first motion determination process, the images may be captured at a low frame rate although the actual motion speed is high, and a situation in which part of the object is not captured may occur. According to the embodiments of the invention, since the frame rate is switched to a low frame rate based on the second motion determination process, it is possible to reduce or suppress a situation in which part of the object is not captured.

A situation in which part of the object is not captured easily occurs when the motion speed of the capsule endoscope has increased, and it is desirable to promptly increase the frame rate so as to follow an increase in the motion speed of the capsule endoscope. According to the embodiments of the invention, since the frame rate is switched to a high frame rate based on the first motion determination process, it is possible to increase the frame rate when it is considered that the motion speed of the capsule endoscope has increased, and reduce or suppress a situation in which part of the object is not captured. When the determination is incorrect, the determination result is corrected by the second motion determination process. Therefore, it is possible to prevent a situation in which the images are captured at an unnecessarily high frame rate, and reduce power consumption.

According to the embodiments of the invention, the external device performs the second motion determination process that requires a second processing load. The processing section 120 performs the first motion determination process that requires a first processing load that is lower than the second processing load.

For example, the first motion determination process compares (e.g., calculates the difference in pixel value) two captured images at the same pixel position to calculates the SAD and the like, and determines the motion speed from the SAD and the like (as described later). On the other hand, the second motion determination process performs a block matching process on two images, and determines the motion speed from the matching result on a block basis.

According to this configuration, the processor of the capsule endoscope 100 that has a relatively low processing capacity due to limitations in terms of hardware scale as compared with the external device 200 can perform the first motion determination process, and promptly switch the frame rate. It is also possible to supplement the first motion determination process using the second motion determination process that requires a high processing load, and implement an accurate motion determination process. In the example described above, the first motion determination process merely compares pixel values, and does not require a heavy iterative process (e.g., block matching process). Therefore, the processor of the capsule endoscope 100 that has a relatively low processing capacity due to limitations in terms of hardware scale can perform the first motion determination process.

The capsule endoscope 100 according to the embodiments of the invention may be configured as described below. Specifically, the capsule endoscope 100 according to the embodiments of the invention may include the imaging section 110 that captures time-series captured images, a memory that stores information (e.g., a program and various types of data), and a processor (i.e., a processor including hardware) that operates based on the information stored in the memory. The processor performs a process that performs the first motion determination process with respect to the imaging section 110 based on the captured images to calculate the first motion determination result. The processor performs a communication process that transmits the captured images to the external device 200 that is provided outside the capsule endoscope 100. The external device 200 performs the second motion determination process with respect to the imaging section 110 based on the captured images transmitted from the capsule endoscope 100, and the processor performs a communication process that receives the second motion determination result from the external device 200. The processor performs the process that controls the frame rate of the imaging section 110 based on the first motion determination result and the second motion determination result.

The processor may implement the function of each section by individual hardware, or may implement the function of each section by integrated hardware, for example. For example, the processor may include hardware, and the hardware may include at least one of a circuit that processes a digital signal and a circuit that processes an analog signal. For example, the processor may include one or a plurality of circuit devices (e.g., IC) or one or a plurality of circuit elements (e.g., resistor or capacitor) that are mounted on a circuit board. The processor may be a central processing unit (CPU), for example. Note that the processor is not limited to a CPU. Various types of processors such as a graphics processing unit (GPU) and a digital signal processor (DSP) may also be used. The processor may be a hardware circuit such as an application specific integrated circuit (ASIC). The processor may include an amplifier circuit, a filter circuit, and the like that process an analog signal. The memory may be a semiconductor memory (e.g., SRAM or DRAM), a register, a magnetic storage device (e.g., hard disk drive), or an optical storage device (e.g., optical disk device). For example, the memory stores a computer-readable instruction. Each section of the capsule endoscope 100 (i.e., the processing section 120 included in the capsule endoscope 100) is implemented by causing the processor to execute the instruction. The instruction may be an instruction included in an instruction set that is included in a program, or may be an instruction that causes a hardware circuit included in the processor to operate.

The operation according to the embodiments of the invention is implemented as described below, for example. The time-series captured images are captured by the imaging section 110, and stored in the memory. The processor performs the first motion determination process with respect to the imaging section 110 based on the captured images read from the memory to calculate the first motion determination result, and stores the first motion determination result in the memory. The processor transmits the captured images read from the memory to the external device 200. A processor provided to the external device 200 performs a communication process that receives the captured images transmitted from the capsule endoscope 100, and stores the captured images in a memory provided to the external device 200. The processor provided to the external device 200 performs the second motion determination process with respect to the imaging section 110 based on the captured images read from the memory provided to the external device 200, and stores the second motion determination result in the memory provided to the external device 200. The processor provided to the external device 200 performs a communication process that transmits the second motion determination result read from the memory provided to the external device 200 to the capsule endoscope 100. The processor of the capsule endoscope 100 performs a communication process that receives the second motion determination result from the external device 200, and stores the second motion determination result in the memory. The processor performs the process that controls the frame rate of the imaging section 110 based on the first motion determination result and the second motion determination result read from the memory.

Each section of the capsule endoscope 100 according to the embodiments of the invention (e.g., the processing section 120 included in the capsule endoscope 100) is implemented as a module of a program that operates on the processor. For example, the processing section 120 is implemented as a processing module that performs the first motion determination process with respect to the capsule endoscope 100 based on the captured images to calculate the first motion determination result. Likewise, the communication section 130 is implemented as a communication module that transmits the captured images to the external device 200 that is provided outside the capsule endoscope 100, and receives the second motion determination result that is the result of the second motion determination process with respect to the capsule endoscope 100 that was performed by the external device 200 based on the captured images.

2. First Detailed Configuration 2.1. Endoscope System

Figure 2:
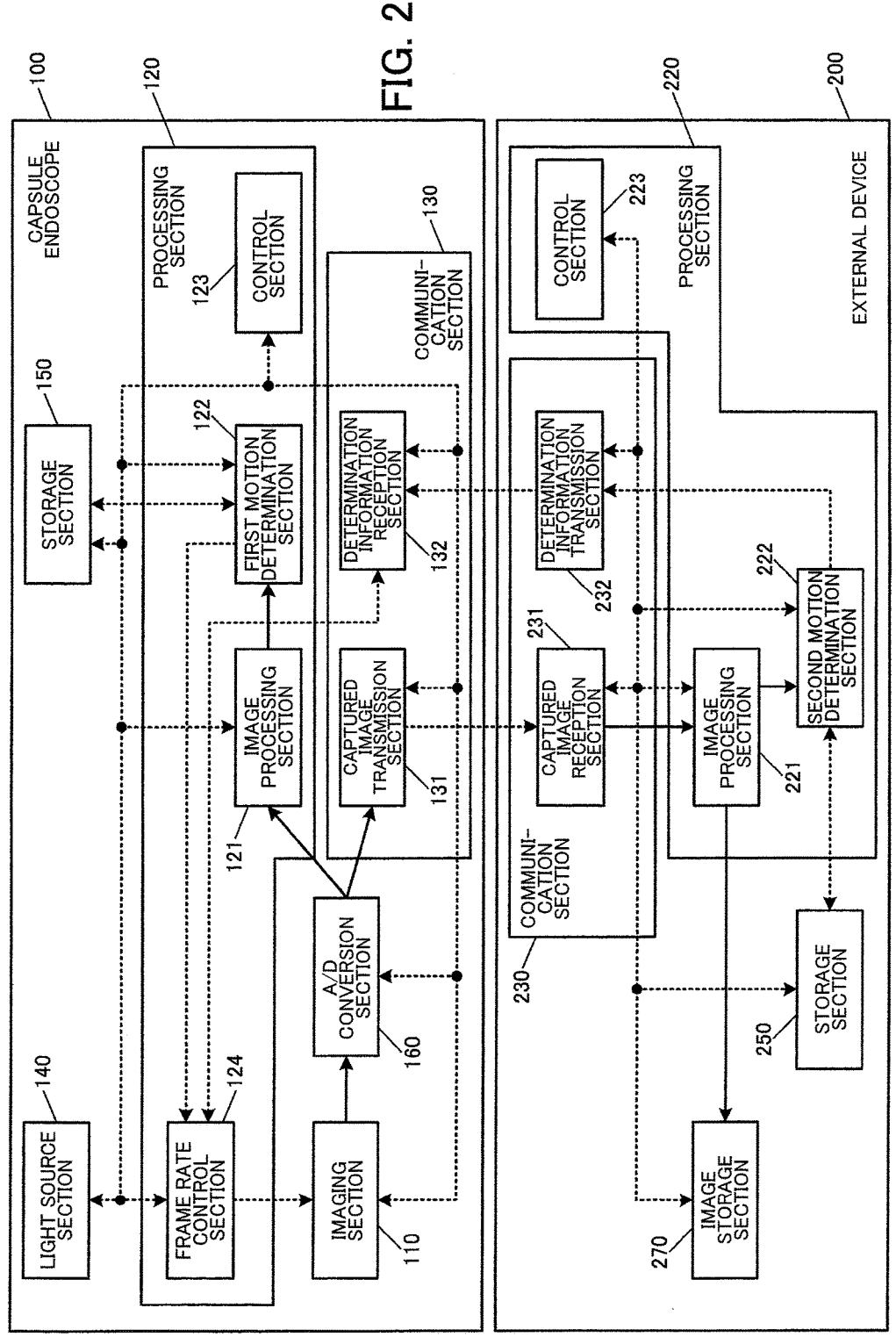
FIG. 2 illustrates a first detailed configuration example of an endoscope system.

The embodiments of the invention are described in detail below. FIG. 2 illustrates a first detailed configuration example of an endoscope system. The endoscope system includes a capsule endoscope 100 (capsule main body) and an external device 200 (extracorporeal device).

The capsule endoscope 100 is an endoscope that is introduced into the body of a patient through swallowing, and sequentially captures the inside of the digestive tract while advancing through the digestive tract due to peristalsis. A plurality of pads (antennas) that exchange a radio wave with the capsule endoscope 100 are attached to the abdomen of the patient. A communication device (receiver device) that communicates with the capsule endoscope 100 is connected to each pad. The communication device is attached to the body of the patient, for example. The external device 200 that performs the second motion determination process corresponds to the communication device, for example. Alternatively, an information processing device (e.g., personal computer (PC)) may be provided separately from the communication device, and may be caused to operate as the external device 200.

The capsule endoscope 100 includes an imaging section 110, a processing section 120, a communication section 130, a light source section 140, a storage section 150, and an A/D conversion section 160. The processing section 120 includes an image processing section 121, a first motion determination section 122, a control section 123, and a frame rate control section 124. The communication section 130 includes a captured image transmission section 131 and a determination information reception section 132.

The external device 200 includes a processing section 220, a communication section 230, a storage section 250, and an image storage section 270. The processing section 220 includes an image processing section 221, a second motion determination section 222, and a control section 223. The communication section 230 includes a captured image reception section 231 and a determination information transmission section 232.

The connection relationship between each section is described below. In the capsule endoscope 100, the imaging section 110 is connected to the A/D conversion section 160. The A/D conversion section 160 is connected to the image processing section 121 and the captured image transmission section 131. The image processing section 121 is connected to the first motion determination section 122. The captured image transmission section 131 is connected to the captured image reception section 231 included in the external device 200 through wireless communication. The storage section 150 is bidirectionally connected to the first motion determination section 122. The first motion determination section 122 and the determination information reception section 132 are connected to the frame rate control section 124. The frame rate control section 124 is connected to the imaging section 110. The control section 123 is bidirectionally connected to the imaging section 110, the A/D conversion section 160, the image processing section 121, the captured image transmission section 131, the first motion determination section 122, the storage section 150, the determination information reception section 132, the frame rate control section 124, and the light source section 140.

In the external device 200, the captured image reception section 231 is connected to the second motion determination section 222 through the image processing section 221. The image processing section 221 is connected to the image storage section 270. The second motion determination section 222 is connected to the determination information transmission section 232. The storage section 250 is bidirectionally connected to the second motion determination section 222. The determination information transmission section 232 is connected to the determination information reception section 132 through wireless communication. The control section 223 is bidirectionally connected to the captured image reception section 231, the image processing section 221, the image storage section 270, the second motion determination section 222, the storage section 250, and the determination information transmission section 232.

2.2. Capsule Endoscope

The process and the operation performed by each section are described below. The capsule endoscope 100 is described below.

Light emitted from the light source section 140 is applied to the object situated outside the capsule endoscope 100 under control of the control section 123. The reflected light from the object passes through an optical lens system included in the imaging section 110 (imaging device) to form an image on an image sensor included in the imaging section 110. The analog captured image output from the image sensor is transmitted to the A/D conversion section 160. For example, the image sensor is a primary-color single-chip (Bayer-array) image sensor.

The A/D conversion section 160 digitizes the analog captured image transmitted from the imaging section 110 under control of the control section 123, and transmits the resulting image to the image processing section 121 and the captured image transmission section 131 as a digital captured image (hereinafter referred to as "captured image").

The image processing section 121 performs image processing on the primary-color single-chip captured image transmitted from the A/D conversion section 160 under control of the control section 123. For example, the image processing section 121 performs a known interpolation process, a known edge enhancement process, a known grayscale transformation process, and the like. In the embodiments of the invention, a known interpolation process is performed on only the G pixel (i.e., G pixels are missing with respect to R pixels and B pixels when a Bayer array is used) of the primary-color single-chip captured image in order to reduce the scale of an image processing circuit provided to the capsule endoscope 100. The interpolation process interpolates the pixel values of the missing G pixels using the average pixel values of the peripheral G pixels. The interpolated captured image (G captured image) that includes only the G pixels is transmitted to the first motion determination section 122. The interpolated G captured image is used for the subsequent motion determination process as a brightness captured image.

It is possible to reduce the implementation scale by causing the image processing section 121 to perform the interpolation process on only the G pixels of the primary-color single-chip captured image as compared with the case of performing the interpolation process on all of the R pixels, the G pixels, and the B pixels. Since the amount of processing on the captured image is reduced, it is possible to reduce the power consumption of the capsule endoscope 100.

Although an example in which the interpolation process is performed on only the G pixels has been described above, another configuration may also be employed. For example, the pixel values of the R pixels and the B pixels may also be interpolated using the average pixel values of the peripheral pixels. In this case, the brightness pixel value Y(x, y) of each pixel is calculated using the following expression (1). The image processing section 121 transmits the brightness image to the first motion determination section 122 under control of the control section 123.

$$Y(x,y)=a1*R(x,y)+b1*G(x,y)+c1*B(x,y) \qquad (1)$$

where, x is the horizontal coordinate value (e.g., the coordinate value in the horizontal scan direction) of the two-dimensional captured image, and y is the vertical coordinate value (e.g., the coordinate value in the vertical scan direction) of the two-dimensional captured image. Y(x, y) is the brightness pixel value of the captured image at the coordinates (x, y). R(x, y) is the R pixel value of the captured image at the coordinates (x, y), G(x, y) is the G pixel value of the captured image at the coordinates (x, y), and B(x, y) is the B pixel value of the captured image at the coordinates (x, y). a1, b1, and c1 are given coefficients for calculating the brightness pixel value Y(x, y).

Figure 3:
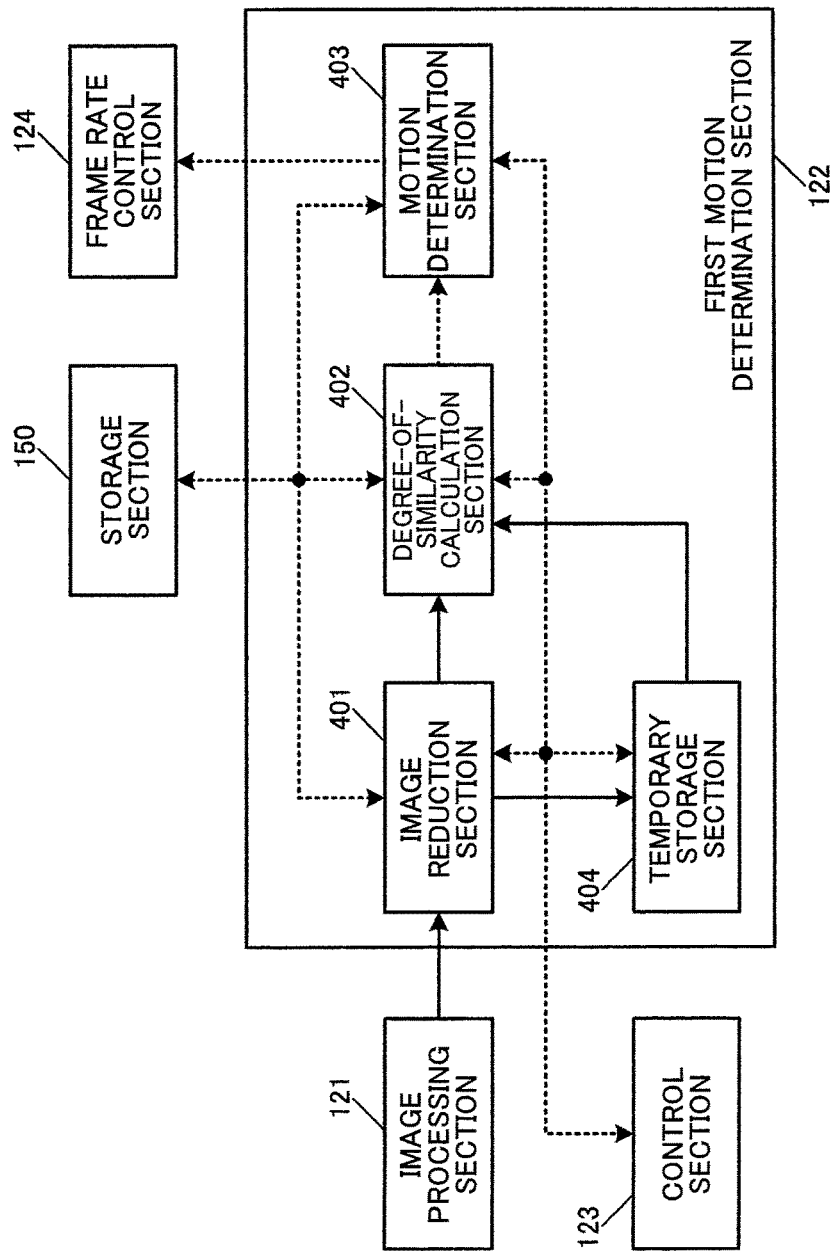
FIG. 3 illustrates a detailed configuration example of a first motion determination section.

FIG. 3 illustrates a detailed configuration example of the first motion determination section 122. The first motion determination section 122 includes an image reduction section 401, a degree-of-similarity calculation section 402, a motion determination section 403, and a temporary storage section 404.

The image processing section 121 is connected to the motion determination section 403 through the image reduction section 401 and the degree-of-similarity calculation section 402. The image reduction section 401 is connected to the temporary storage section 404. The storage section 150 is bidirectionally connected to the image reduction section 401, the degree-of-similarity calculation section 402, and the motion determination section 403. The motion determination section 403 is connected to the frame rate control section 124. The control section 123 is bidirectionally connected to the image reduction section 401, the degree-of-similarity calculation section 402, the motion determination section 403, and the temporary storage section 404.

The image reduction section 401 performs a reduction process on the image (i.e., the interpolated captured image that includes only the G pixels (hereinafter referred to as "G captured image")) transmitted from the image processing section 121 under control of the control section 123. In the embodiments of the invention, a thinning process is performed on the G captured image to reduce the size of the G captured image. Note that the G captured image that has been reduced in size is hereinafter referred to as "reduced G captured image".

More specifically, the skip width size and the skip height size used for the thinning process performed on the G captured image are calculated using the following expression (2).

StepWidth=Width/ReduceWidth,

StepHeight=Height/ReduceHeight    (2)

where, Width is the width of the G captured image, and Height is the height of the G captured image. ReduceWidth is the width of the reduced G captured image, and ReduceHeight is the height of the reduced G captured image. StepWidth is the thinning interval (skip width size) in the horizontal axis direction, and StepHeight is the thinning interval (skip height size) in the vertical axis direction.

The parameters Width, Height, ReduceWidth, and ReduceHeight are stored in the storage section 150 (memory) in advance. The image reduction section 401 reads the parameters Width, Height, ReduceWidth, and ReduceHeight from the storage section 150 under control of the control section 123 when performing the reduction process.

Note that the parameters StepWidth and StepHeight may be stored in the storage section 150 in advance. In this case, the reduction process can be performed without calculating the parameters StepWidth and StepHeight using the expression (1).

The image reduction section 401 selects (skips) the pixel of the G captured image using the skip width size StepWidth (in the horizontal axis direction) and the skip height size StepHeight (in the vertical axis direction) under control of the control section 123, and generates a reduced captured image using the selected pixels. The skip process is performed using the upper left pixel of the G captured image as a reference, for example.

Although an example in which the thinning reduction process is performed has been described above, another configuration may also be employed. For example, a block area having a given size (e.g., 3×3 or 5×5) may be set around each pixel selected by the skip process, a known averaging process or weighted averaging process may be performed on all of the pixel values within the block area, and the reduced captured image may be generated using the resulting pixel value as the pixel value of each pixel selected by the skip process.

The image reduction section 401 transmits the reduced G captured image obtained by the reduction process to the degree-of-similarity calculation section 402 and the temporary storage section 404 (memory) under control of the control section 123. The previous reduced G captured image on a time-series basis is stored in the temporary storage section 404, and used to calculate the degree of similarity with the subsequent reduced G captured image on a time-series basis. More specifically, the oldest reduced G captured image stored in the temporary storage section 404 is updated each time the reduced G captured image is acquired in time series, and the acquired (current) reduced G captured image is stored in the temporary storage section 404.

In the embodiments of the invention, the degree of similarity between the current reduced G captured image and the previous reduced G captured image on a time-series basis is calculated, and the presence or absence of a physical motion of the capsule endoscope 100, the object, or the like (hereinafter may be referred to as "physical motion of the capsule") is determined based on the degree of similarity. The motion determination process is described below.

The degree-of-similarity calculation section 402 calculates the sum of absolute difference (SAD) value by the following expression (3) under control of the control section 123 using the current reduced G captured image transmitted from the image reduction section 401 and the previous reduced G captured image transmitted from the temporary storage section 404. The degree of similarity between the two reduced G captured images is determined to be higher as the SAD value is closer to 0. The degree-of-similarity calculation section 402 transmits an isad value to the motion determination section 403 under control of the control section 123.

$$isad=\Sigma_{j=0}^{N-1}\Sigma_{i=0}^{M-1}(|I(i,j)-I'(i,j)|) \quad (3)$$

where, isad is the SAD value. i is the horizontal coordinate value of the reduced G captured image, and j is the vertical coordinate value of the reduced G captured image. M is the width of the reduced G captured image, and N is the height of the reduced G captured image. I(i, j) is the pixel value of the current reduced G captured image at the coordinates (i, j), and I'(i, j) is the pixel value of the previous reduced G captured image at the coordinates (i, j).

Although an example in which the SAD value is calculated from two time-series captured images to determine the degree of similarity has been described above, another configuration may also be employed. For example, the sum of squared difference (SSD) value may be calculated using the following expression (4) to determine the degree of similarity, or the normalized cross-correction (NCC) value may be calculated using the following expression (5) to determine the degree of similarity.

$$issd=\Sigma_{j=0}^{N-1}\Sigma_{i=0}^{M-1}(I(i,j)-I'(i,j))^2 \quad (4)$$

$$incc=\frac{\Sigma_{j=0}^{N-1}\Sigma_{i=0}^{M-1}(I(i,j)*I'(i,j))/}{\sqrt{\Sigma_{j=0}^{N-1}\Sigma_{i=0}^{M-1}(I(i,j))^2 * \Sigma_{j=0}^{N-1}\Sigma_{i=0}^{M-1}(I'(i,j))^2}} \quad (5)$$

where, issd is the SSD value, incc is the NCC value, and i, j, M, N, I(i, j), and I'(i, j) are the same as defined above in connection with the expression (3).

Although an example in which the degree of similarity is calculated from two captured images that are contiguous to each other on a time-series basis has been described above, another configuration may also be employed. For example, the captured images may be skipped at a given interval (time or number of frames), and the degree of similarity may be calculated from two captured images that are not contiguous to each other on a time-series basis. For example, when the skip interval is set to 1, two images that were captured at an interval of one image are used to calculate the degree of similarity. Specifically, the degree of similarity is calculated using the current captured image and the second captured image that precedes the current captured image on a time-series basis. This makes it possible to reduce the amount of processing required for the motion determination process by a factor of 1/N (where N is "skip interval+1").

The operation of the motion determination section 403 is described below using an example in which the imaging frame rate can be set to a high-speed frame rate (first frame rate) and a low-speed frame rate (second frame rate).

Figure 4:
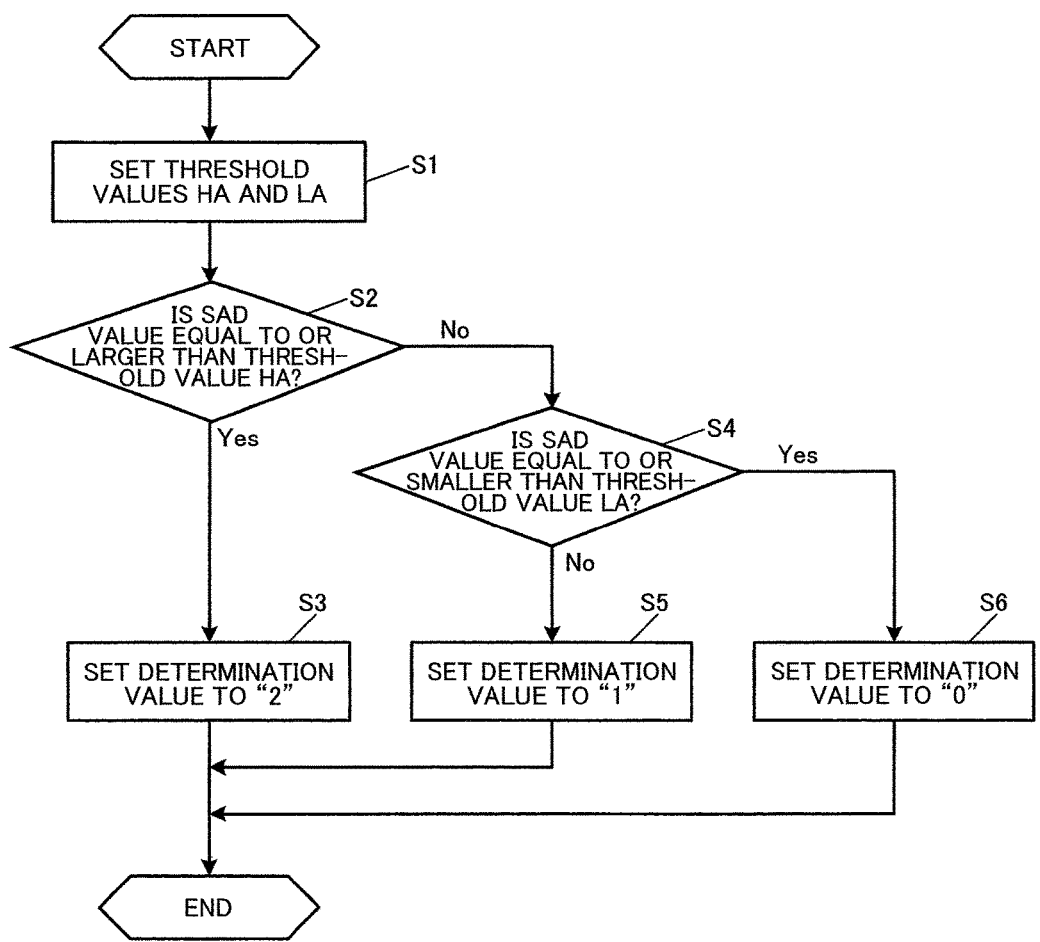
FIG. 4 is a flowchart illustrating a first motion determination process.

FIG. 4 is a flowchart illustrating the first motion determination process. The motion determination section 403 reads a first SAD threshold value HA and a second SAD threshold value LA (HA>LA) used for the motion determination process (that are stored in advance) from the storage section 150 under control of the control section 123 (step S1).

The motion determination section 403 compares the SAD value isad transmitted from the degree-of-similarity calculation section 402 with the threshold values HA and LA. More specifically, the motion determination section 403 determines whether or not the SAD value isad is equal to or larger than the threshold value HA (step S2). When the SAD value isad is equal to or larger than the threshold value HA, the motion determination section 403 sets the determination value (control signal value) of the first motion determination process to "2" (step S3). Specifically, the motion determination section 403 determines that the motion amount is large. When the SAD value isad is smaller than the threshold value HA, the motion determination section 403 determines whether or not the SAD value isad is equal to or smaller than the threshold value LA (step S4). When the SAD value isad is equal to or smaller than the threshold value LA, the motion determination section 403 sets the determination value to "0" (step S6). Specifically, the motion determination section 403 determines that the motion amount is small. When the SAD value isad is equal to or larger than the threshold value LA, the motion determination section 403 sets the determination value to "1" (step S5). Specifically, the motion determination section 403 determines that the motion amount is moderate. The motion determination section 403 transmits the determination value to the frame rate control section 124.

Note that the imaging frame rate is switched to the high-speed frame rate when the determination value is "2", is maintained when the determination value is "1", and is switched to the low-speed frame rate when the determination value is "0" (as described later).

As described above, since the first motion determination process part 122 calculates the degree of similarity from the G captured image that has been reduced in the number of pixels through the reduction process, it is possible to reduce the processing load during the motion determination process. This makes it possible to reduce the implementation scale of the capsule endoscope 100. Since the amount of processing on the captured image is reduced, it is possible to reduce the power consumption of the capsule endoscope 100.

Although an example in which the degree-of-similarity calculation process and the motion determination process are performed after reducing the size of the G captured image has been described above, another configuration may also be employed. For example, the degree-of-similarity calculation process and the motion determination process may be performed without reducing the size of the G captured image. In this case, since a high-load process such as a block matching process is not performed when calculating the degree of similarity (e.g., using the expression (3)), it is possible to save the processing capacity of the processor. The thinning interval StepWidth in the horizontal axis direction and the thinning interval StepHeight in the vertical axis direction may be controlled to be given values without interpolating the G captured image, and the G pixels of a primary-color Bayer array may be extracted to implement the reduction process.

2.3. External Device

The process and the operation performed by each section of the external device 200 are described below. Note that the frame rate control section 124 of the capsule endoscope 100 controls the frame rate using the second motion determination result from the external device 200. Therefore, the details of the frame rate control section 124 are described later.

The captured image reception section 231 receives the captured image transmitted from the capsule endoscope 100 through wireless communication, and transmits the captured image to the image processing section 221 and the image storage section 270 (memory). The image storage section 270 stores the captured image.

The image processing section 221 performs image processing on the captured image transmitted from the captured image reception section 231 under control of the control section 223. For example, the image processing section 221 performs a known interpolation process, a known color management process, a known edge enhancement process, a known grayscale transformation process, and the like. The image processing section 221 transmits the resulting RGB captured image (i.e., an image in which each pixel has RGB pixel values) to the image storage section 270 under control of the control section 223. The image storage section 270 stores the RGB captured image. The image storage section 270 calculates the brightness pixel value from the RGB captured image using the expression (1). The image storage section 270 transmits the captured image having the brightness pixel values (hereinafter referred to as "brightness image") to the second motion determination section 222 under control of the control section 223.

Figure 5:
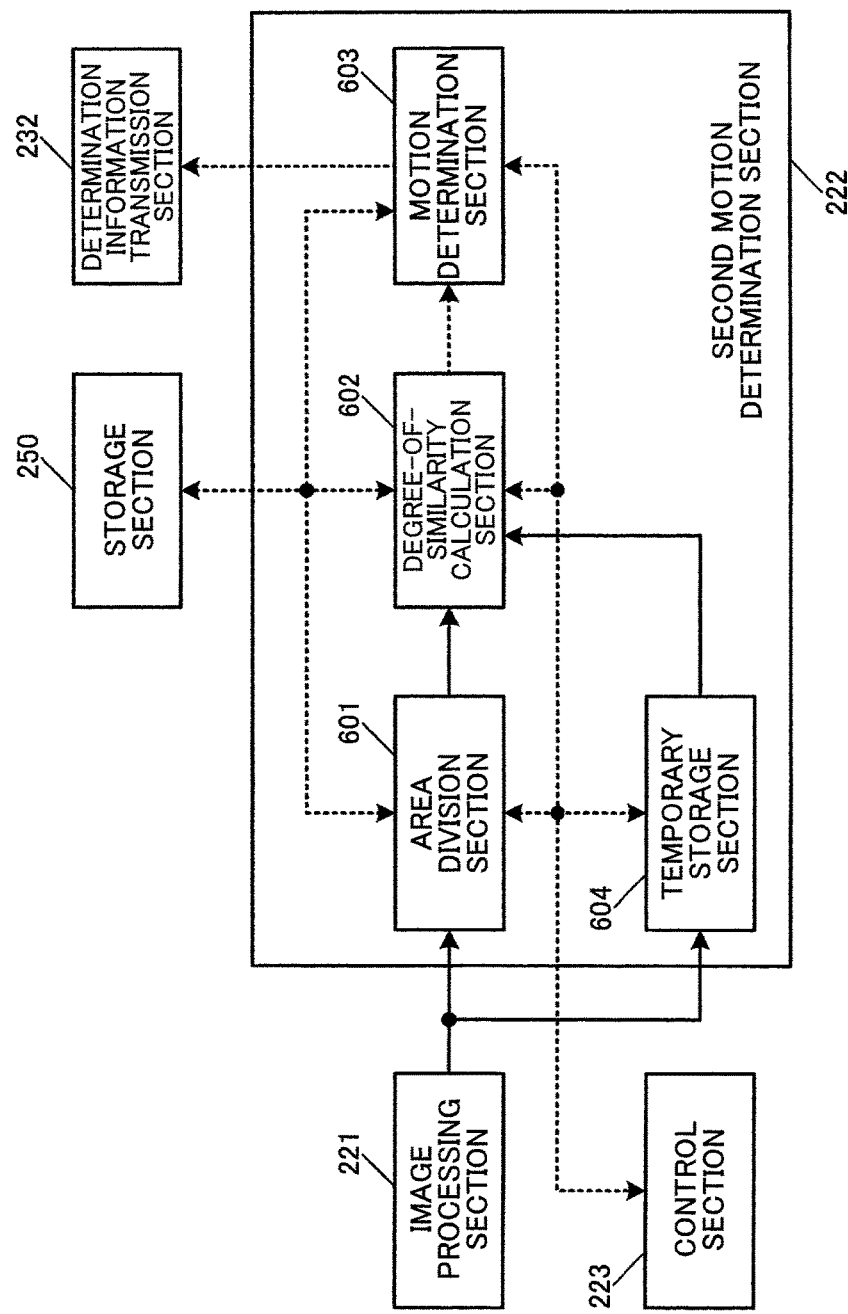
FIG. 5 illustrates a detailed configuration example of a second motion determination section.

FIG. 5 illustrates a detailed configuration example of the second motion determination section 222. The second motion determination section 222 includes an area division section 601, a degree-of-similarity calculation section 602, a motion determination section 603, and a temporary storage section 604.

The image processing section 221 is connected to the motion determination section 603 through the area division section 601 and the degree-of-similarity calculation section 602. The image processing section 221 is connected to the temporary storage section 604. The storage section 250 is bidirectionally connected to the area division section 601, the degree-of-similarity calculation section 602, and the motion determination section 603. The motion determination section 603 is connected to the determination information transmission section 232. The control section 223 is bidirectionally connected to the area division section 601, the degree-of-similarity calculation section 602, the motion determination section 603, and the temporary storage section 604.

The brightness image is transmitted from the image processing section 221 to the area division section 601 and the temporary storage section 604 (memory) under control of the control section 223. The previous brightness image on a time-series basis is stored in the temporary storage section 604, and used to calculate the degree of similarity with the subsequent brightness image on a time-series basis. The temporary storage section 604 deletes the oldest brightness image each time the brightness image is acquired in time series, and stores the acquired current brightness image.

The area division section 601 divides the current brightness image transmitted from the image processing section 221 into a plurality of block areas based on information about the block area size stored in the storage section 250 (memory), and transmits the divided brightness image to the degree-of-similarity calculation section 602.

The degree-of-similarity calculation section 602 performs a template matching process (e.g., SAD, SSD, or NCC) on the brightness image of each block area transmitted from the area division section 601 and the previous brightness image transmitted from the temporary storage section 604 based on information about the detection area size used for the template matching process that is stored in the storage section 250.

Figure 6:
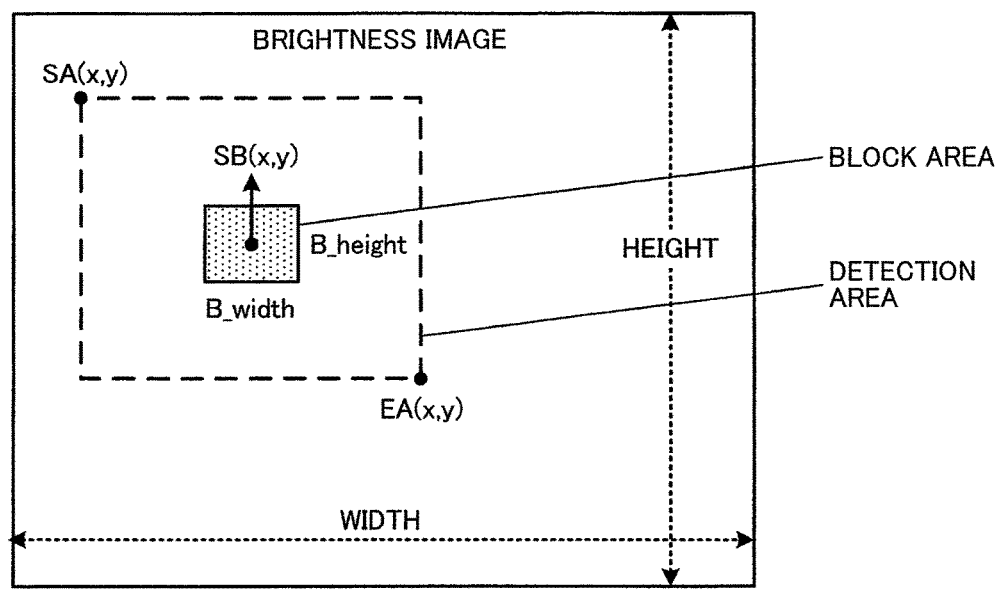
FIG. 6 is a view illustrating an example of a template matching process.

FIG. 6 illustrates an example of the template matching process. In FIG. 6, the image size of the brightness image is represented by a height HEIGHT and a width WIDTH, and the size of the block area is represented by a height B_height and a width B_width.

The degree-of-similarity calculation section 602 detects the motion amount of the block area under control of the control section 223 using a block center point SB(x, y) as a block representative point. In this case, the degree-of-similarity calculation section 602 performs the template matching process on an attention block area and the detection area. The term "attention block area" used herein refers to the current processing target block area among a plurality of block areas that are sequentially subjected to the template matching process. The detection area is an area that has been set to the previous brightness image using size information transmitted from the storage section 250. The size information includes start coordinates SA(x, y) and end coordinates EA(x, y) of the detection area. The height and the width of the detection area are respectively larger than the height and the width of the block area.

The degree-of-similarity calculation section 602 calculates the SAD value when the upper left pixel of the attention block area and the upper left pixel (SA(x, y)) of the detection area are allowed to coincide with each other using the expression (3). The degree-of-similarity calculation section 602 performs this process while shifting the attention block area by one pixel in the rightward direction or the downward direction with respect to the detection area to calculate the SAD value corresponding to all of the pixels within the detection area. The degree-of-similarity calculation section 602 extracts the minimum SAD value from the SAD values thus calculated, and determines the minimum SAD value to be a representative SAD value of the attention block area. The degree-of-similarity calculation section 602 performs this process corresponding to each block area to calculate the representative SAD value of each block area, and transmits the representative SAD values to the motion determination section 603.

Figure 7:
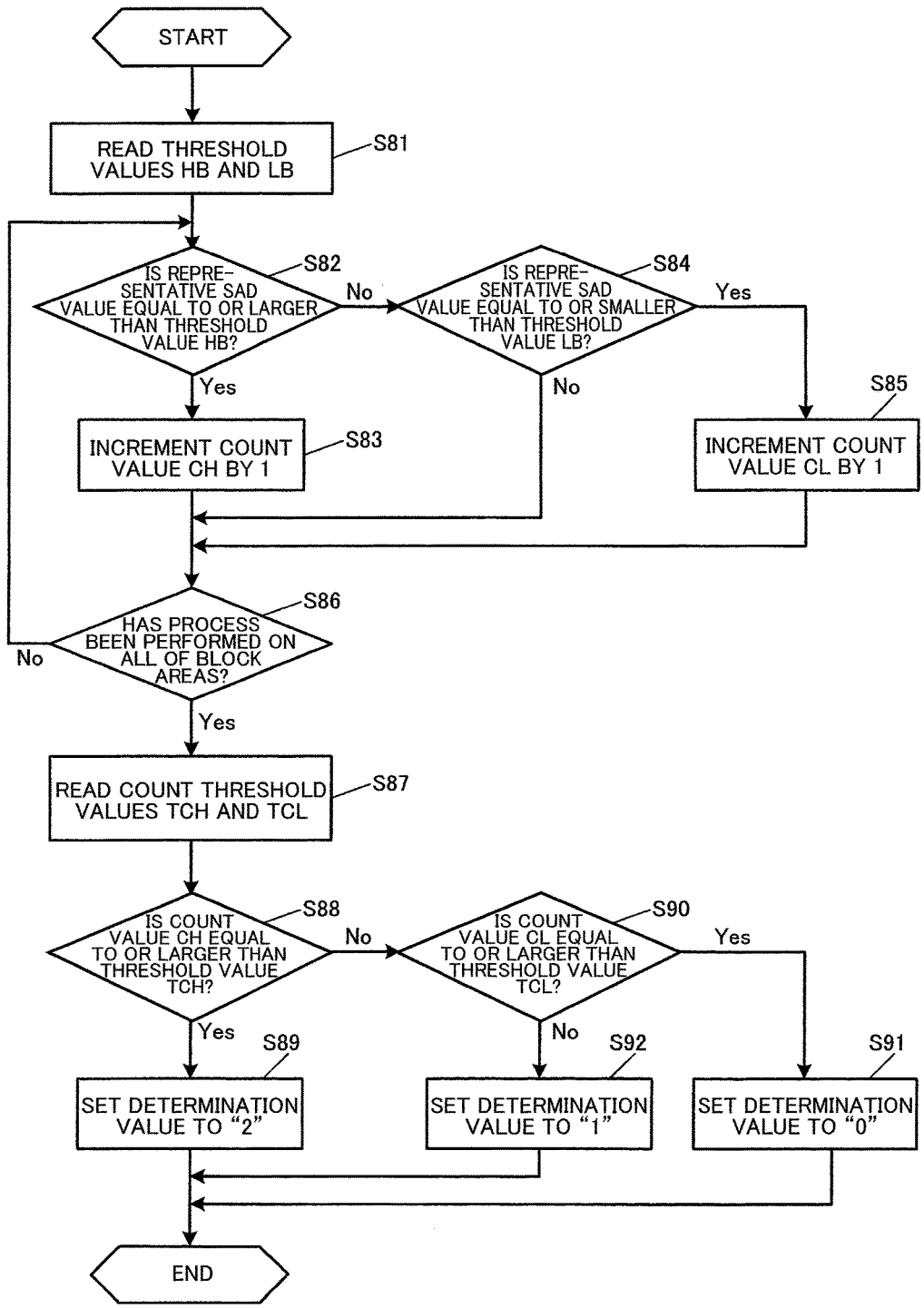
FIG. 7 is a flowchart illustrating a second motion determination process.

The operation of the motion determination section 603 is described below. FIG. 7 is a flowchart illustrating the second motion determination process. The motion determination section 603 reads a third SAD threshold value HB and a fourth SAD threshold value LB (HB>LB) used for the motion determination process (that are stored in advance) from the storage section 250 under control of the control section 223 (step S81). Note that the threshold values HB and LB may be identical to the threshold values HA and LA, and may be different from the threshold values HA and LA.

The motion determination section 603 compares the representative SAD value of each block area transmitted from the degree-of-similarity calculation section 602 with the threshold values HB and LB. More specifically, the motion determination section 603 determines whether or not the representative SAD value is equal to or larger than the threshold value HB (step S82). When the representative SAD value is equal to or larger than the threshold value HB, the motion determination section 603 increments a first count value CH used for the motion determination process by 1 (step S83). Note that the initial value of the count value CH is 0. When the representative SAD value is smaller than the threshold value HB, the motion determination section 603 determines whether or not the representative SAD value is equal to or smaller than the threshold value LB (step S84). When the representative SAD value is equal to or smaller than the threshold value LB, the motion determination section 603 increments a second count value CL used for the motion determination process by 1 (step S85). When the representative SAD value is larger than the threshold value LB, the motion determination section 603 does not change the count values CH and CL. When the process has not been performed on all of the block areas, the motion determination section 603 performs the step S82 again. When the process has been performed on all of the block areas, the motion determination section 603 performs a step S87 (step S86).

The motion determination section 603 reads a first count threshold value TCH used for the count value CH and a second count threshold value TCL used for the count value CL (TCH>TCL) (that are stored in advance) from the storage section 250 (step S87).

The motion determination section 603 compares the count values CH and CL with the count threshold values TCH and TCL. More specifically, the motion determination section 603 determines whether or not the count value CH is equal to or larger than the count threshold value TCH (step S88). When the count value CH is equal to or larger than the count threshold value TCH, the motion determination section 603 sets the determination value of the second motion determination process to "2". Specifically, the motion determination section 603 determines that the motion amount is large. When the count value CH is smaller than the count threshold value TCH, the motion determination section 603 determines whether or not the count value CL is equal to or larger than the count threshold value TCL (step S90). When the count value CL is equal to or larger than the count threshold value TCL, the motion determination section 603 sets the determination value to "0" (step S91). Specifically, the motion determination section 603 determines that the motion amount is small. When the count value CL is smaller than the count threshold value TCL, the motion determination section 603 sets the determination value to "1" (step S92). Specifically, the motion determination section 603 determines that the motion amount is moderate. The motion determination section 603 transmits the determination value to the determination information transmission section 232, and the determination information transmission section 232 transmits the determination value to the determination information reception section 132 through wireless communication.

Note that the imaging frame rate is switched to the high-speed frame rate when the determination value is "2", and is switched to the low-speed frame rate when the determination value is "0" (as described later). The imaging frame rate is switched corresponding to the current frame rate when the determination value is "1".

As described above, the determination value is set to "2" when the count value CH is equal to or larger than the count threshold value TCH, set to "0" when the count value CL is equal to or larger than the count threshold value TCL, and set to "1" when the count value CH is smaller than the count threshold value TCH, and the count value CL is smaller than the count threshold value TCL.

There may be a case where the count value CH is equal to or larger than the count threshold value TCH, and the count value CL is equal to or larger than the count threshold value TCL. In such a case, the process is performed as described below.

Specifically, the first count threshold value TCH and the second count threshold value TCL are set so that the relationships "number of block areas≥first count threshold value TCH≥1" and "number of block areas≥second count threshold value TCL≥1" are satisfied. The first count threshold value TCH is a threshold value for determining the number of block areas in which the physical motion of the capsule endoscope 100 is large. Therefore, when the first count threshold value TCH is set to a small value, it is likely that the frame rate is switched to the high-speed frame rate (determination value: "2"). On the other hand, the second count threshold value TCL is a threshold value for determining the number of block areas in which the physical motion of the capsule endoscope 100 is small. Therefore, when the second count threshold value TCL is set to a large value, it is likely that the frame rate is switched to the low-speed frame rate (determination value: "0").

The desired count threshold values are set using the above characteristics. However, the condition whereby the determination value is set to "2" and the condition whereby the determination value is set to "0" may be satisfied at the same time depending on the first count threshold value TCH and the second count threshold value TCL. In order to prevent the occurrence of such a situation, it is desirable to experimentally set the first count threshold value TCH and the second count threshold value TCL in advance, for example. If the condition whereby the determination value is set to "2" and the condition whereby the determination value is set to "0" have been satisfied at the same time, it is desirable to set the determination value to "2" from the viewpoint of suppressing the occurrence of an incorrect diagnosis. In the flowchart illustrated in FIG. 7, since the count value CH and the count threshold value TCH are compared in the step S88, priority is given to the determination value "2".

As described above, since the external device 200 is relatively less limited in terms of hardware scale as compared with the capsule endoscope 100, the external device 200 can perform the template matching process. The external device 200 can count the number of block areas in which the motion amount is determined to be large, and the number of block areas in which the motion amount is determined to be small, from the results of the template matching process, and determine the motion of the capsule endoscope 100 from the count values. This makes it possible to implement a motion determination process that is more accurate than the first motion determination process performed by the capsule endoscope 100.

2.4. Frame Rate Control Section

Figure 8:
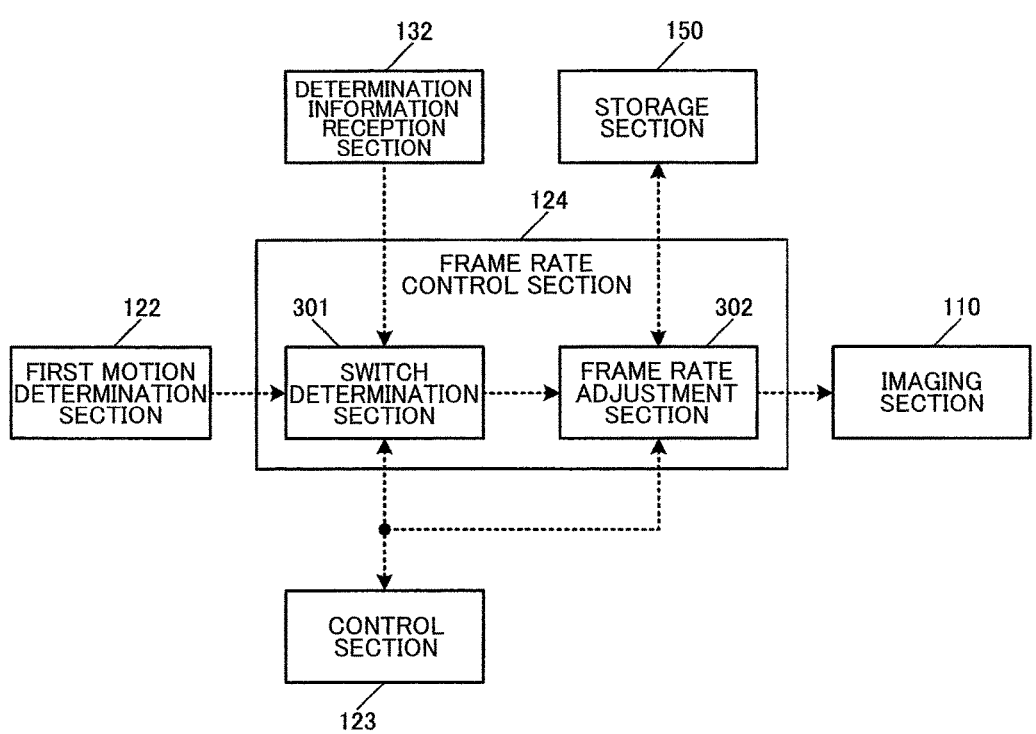
FIG. 8 illustrates a detailed configuration example of a frame rate control section.

The operation of the frame rate control section 124 included in the capsule endoscope 100 is described below. FIG. 8 illustrates a detailed configuration example of the frame rate control section 124. The frame rate control section 124 includes a switch determination section 301 and a frame rate adjustment section 302.

The first motion determination section 122 is connected to the imaging section 110 through the switch determination section 301 and the frame rate adjustment section 302. The determination information reception section 132 is connected to the switch determination section 301. The storage section 150 is bidirectionally connected to the frame rate adjustment section 302. The control section 123 is bidirectionally connected to the switch determination section 301 and the frame rate adjustment section 302.

Figure 9:
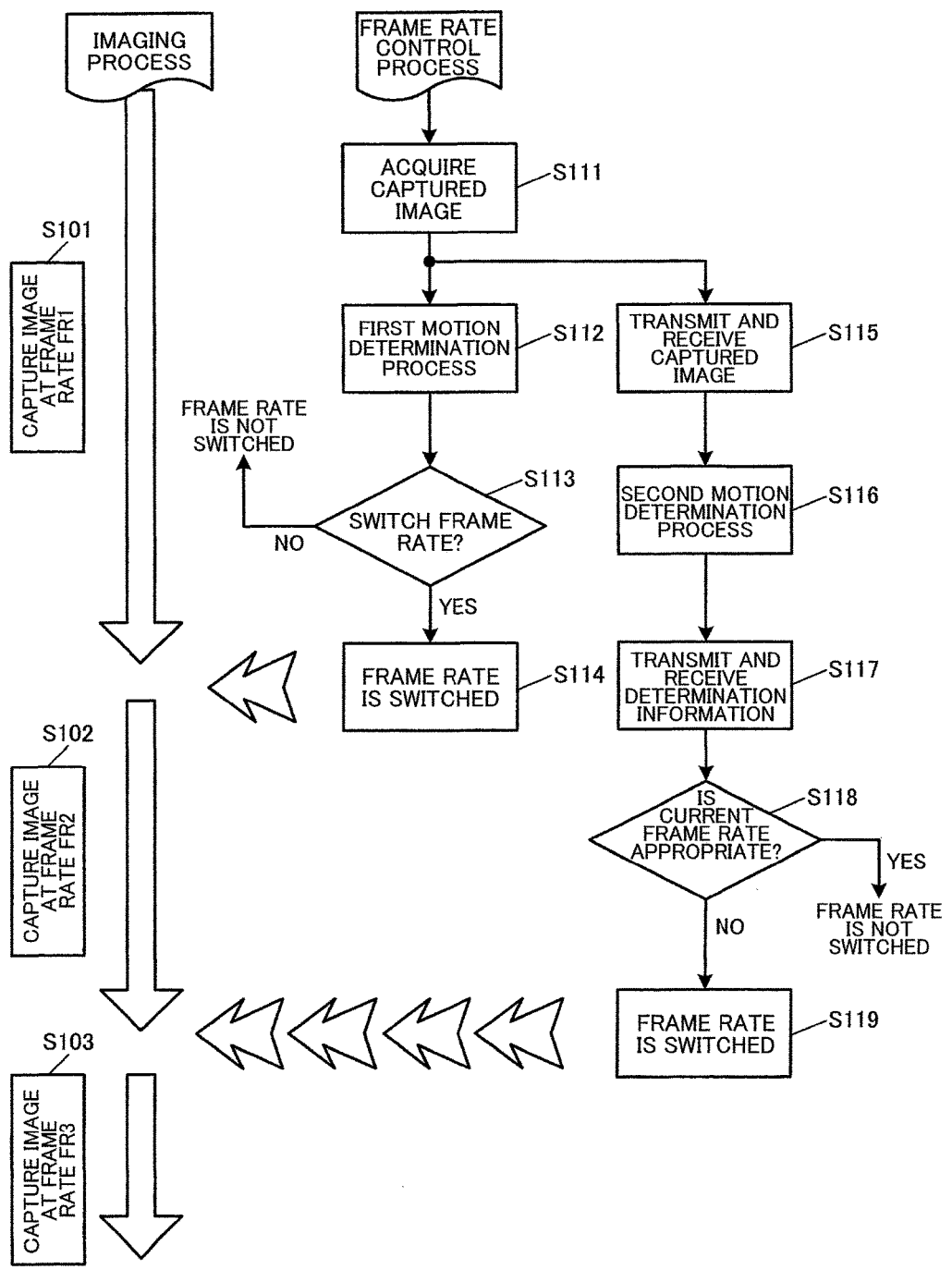
FIG. 9 is a flowchart illustrating a frame rate control process.

FIG. 9 is a flowchart illustrating a frame rate control process. The first motion determination section 122 and the captured image transmission section 131 acquire the captured image from the image processing section 121 (step S111).

The first motion determination section 122 included in the capsule endoscope 100 performs the first motion determination process (step S112). The switch determination section 301 determines whether or not to switch the frame rate under control of the control section 123 (step S113). When it has been determined to switch the frame rate, the frame rate adjustment section 302 switches the frame rate of the imaging section 110 (step S114). Specifically, when the current frame rate is a frame rate FR1 (e.g., low-speed frame rate) (see step S101), the frame rate adjustment section 302 switches the frame rate to a frame rate FR2 (e.g., high-speed frame rate) (see step S102).

The captured image reception section 231 included in the external device 200 receives the captured image, and the second motion determination section 222 acquires the captured image from the captured image reception section 231 (step S115). The second motion determination section 222 performs the second motion determination process (step S116). The determination information transmission section 232 transmits the result of the second motion determination process to the determination information reception section 132 (step S117). The switch determination section 301 determines whether or not the frame rate switch control process (current frame rate) based on the result of the first motion determination process is appropriate under control of the control section 123 (step S118). When it has been determined that the frame rate switch control process based on the result of the first motion determination process is appropriate, the frame rate adjustment section 302 maintains the current frame rate. When it has been determined that the frame rate switch control process based on the result of the first motion determination process is not appropriate, the frame rate adjustment section 302 switches the frame rate of the imaging section 110 (step S119). Specifically, when the current frame rate is the frame rate FR2 (e.g., high-speed frame rate) (see step S102), the frame rate adjustment section 302 switches the frame rate to a frame rate FR3 (e.g., low-speed frame rate) (see step S103).

Figure 10:
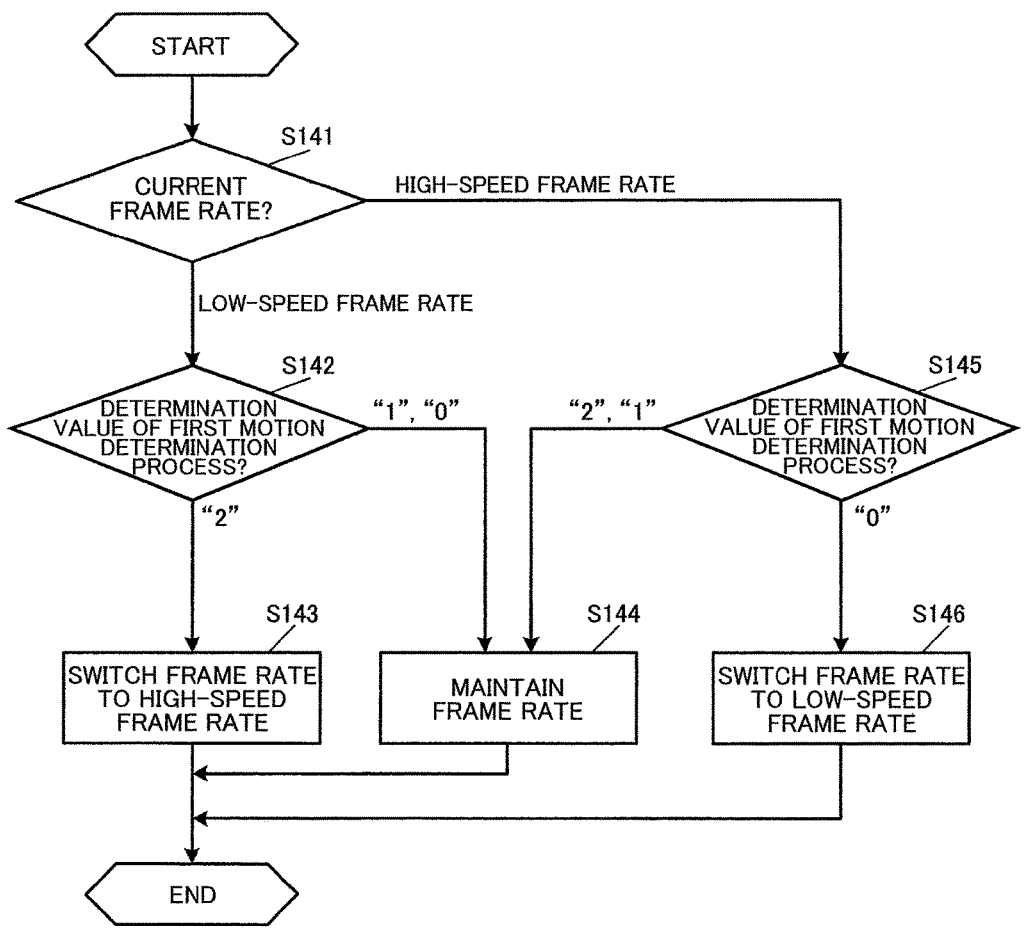
FIG. 10 is a flowchart illustrating a frame rate switch process based on a first motion determination process.

The frame rate switch determination process performed in the steps S113 and S118 is described in detail below. FIG. 10 is a flowchart illustrating the frame rate switch determination process based on the first motion determination process (step S113).

The control process is performed as described below when the current frame rate is the low-speed frame rate (step S141). The switch determination section 301 determines that it is necessary to switch the frame rate when the determination value is "2" (step S142), and switches the frame rate to the high-speed frame rate (step S143). The switch determination section 301 determines that it is unnecessary to switch the frame rate when the determination value is "1" or "0" (step S142), and maintains the low-speed frame rate (step S144).

The control process is performed as described below when the current frame rate is the high-speed frame rate (step S141). The switch determination section 301 determines that it is necessary to switch the frame rate when the determination value is "0" (step S145), and switches the frame rate to the low-speed frame rate (step S146). The switch determination section 301 determines that it is unnecessary to switch the frame rate when the determination value is "2" or "1" (step S145), and maintains the high-speed frame rate (step S144).

As described above, the frame rate is switched to the high-speed frame rate (or maintained) when the determination value is "2", is maintained when the determination value is "1", and is switched to the low-speed frame rate (or maintained) when the determination value is "0".

Figure 11:
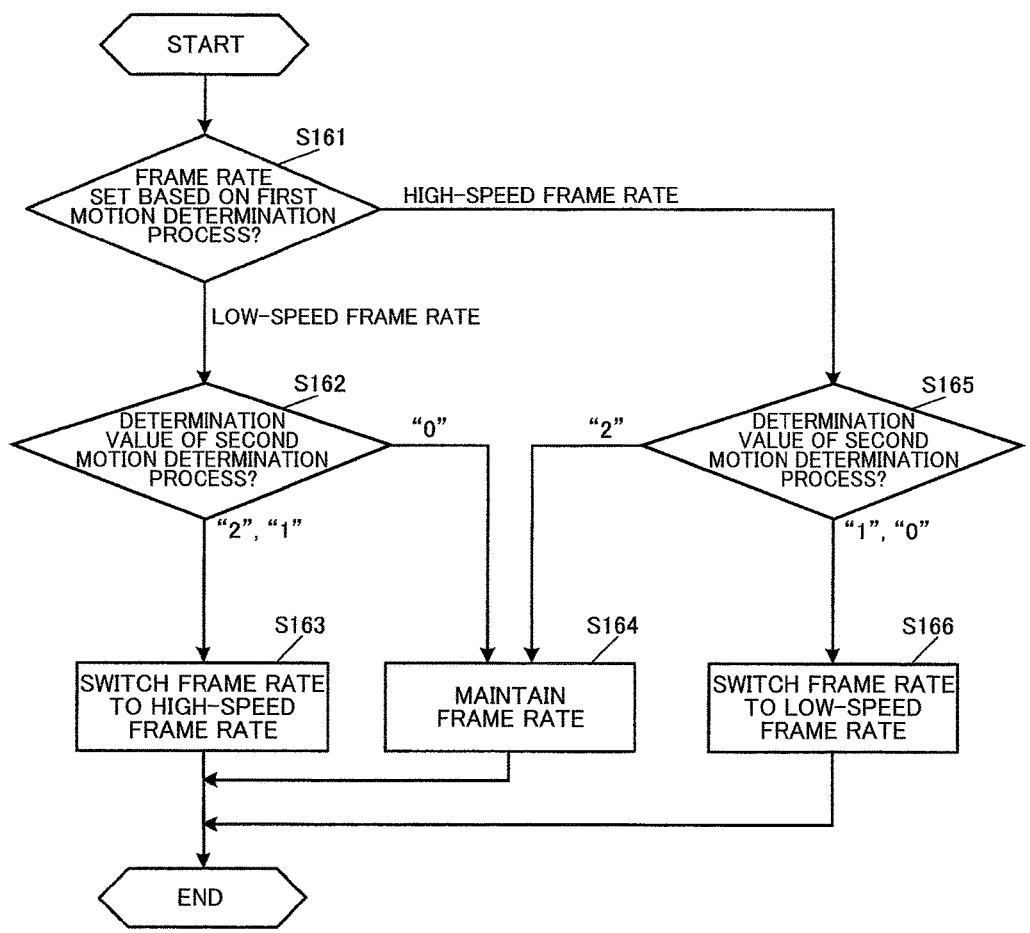
FIG. 11 is a flowchart illustrating a frame rate switch process based on a second motion determination process.

FIG. 11 is a flowchart illustrating the frame rate switch determination process based on the second motion determination process (step S117).

The control process is performed as described below when the frame rate has been set to the low-speed frame rate as a result of the first motion determination process (step S161). The switch determination section 301 determines that the frame rate that has been set as a result of the first motion determination process is not appropriate when the determination value is "2" or "1" (step S162), and switches the frame rate to the high-speed frame rate (step S163). The switch determination section 301 determines that the frame rate that has been set as a result of the first motion determination process is appropriate when the determination value is "0" (step S162), and maintains the low-speed frame rate (step S164).

The control process is performed as described below when the frame rate has been set to the high-speed frame rate as a result of the first motion determination process (step S161). The switch determination section 301 determines that the frame rate that has been set as a result of the first motion determination process is not appropriate when the determination value is "1" or "0" (step S165), and switches the frame rate to the low-speed frame rate (step S166). The switch determination section 301 determines that the frame rate that has been set as a result of the first motion determination process is appropriate when the determination value is "2" (step S165), and maintains the high-speed frame rate (step S164).

As described above, the current frame rate is maintained when the determination value of the second motion determination process agrees with the frame rate set based on the first motion determination process, and is switched to the high-speed frame rate or the low-speed frame rate when the determination value of the second motion determination process does not agree with the frame rate set based on the first motion determination process.

According to the embodiments of the invention, the processing section 120 switches the frame rate to the high-speed frame rate (step S3 and FIG. 10 (flowchart)) when it has been determined by the first motion determination process (FIG. 4 (flowchart)) that the motion amount (SAD value isad) of the object captured within the captured image is larger than a first motion amount (threshold value HA) (step S2). The processing section 120 switches the frame rate to the low-speed frame rate that is lower than the high-speed frame rate (step S6 and FIG. 10 (flowchart)) when it has been determined by the first motion determination process that the motion amount is smaller than a second motion amount (threshold value LA<HA) that is smaller than the first motion amount (step S4).

According to this configuration, it is possible to determine the speed of the motion of the capsule endoscope 100 by determining the motion amount using the first motion amount and the second motion amount. It is also possible to determine a case where the motion speed has relatively increased with respect to the current frame rate (determination value: "2"), a case where the motion speed is appropriate with respect to the current frame rate (determination value: "1"), and a case where the motion speed has relatively decreased with respect to the current frame rate (determination value: "0"). Specifically, it is possible to switch the frame rate corresponding to a relative change in motion speed.

According to the embodiments of the invention, the processing section 120 switches the frame rate to the high-speed frame rate (step S163 illustrated in FIG. 11) when the second motion determination process has determined that the motion amount is larger than a third motion amount (step S89 illustrated in FIG. 7 and step S162 illustrated in FIG. 11) in a state in which the frame rate is set to the low-speed frame rate (step S161 illustrated in FIG. 11). The processing section 120 switches the frame rate to the low-speed frame rate (step S163 illustrated in FIG. 11) when the second motion determination process has determined that the motion amount is smaller than a fourth motion amount that is smaller than the third motion amount (step S91 illustrated in FIG. 7 and step S165 illustrated in FIG. 11) in a state in which the frame rate is set to the high-speed frame rate (step S161 illustrated in FIG. 11).

According to this configuration, it is possible to determine whether or not the frame rate set based on the first motion determination process is appropriate by determining the motion amount using the third motion amount and the fourth motion amount. Specifically, it is possible to switch the frame rate when the motion speed (determination value) determined by the second motion determination process does not agree with the frame rate set based on the first motion determination process.

In the second motion determination process illustrated in FIG. 7 (flowchart), the count values CH and CL are used as the information that represents the motion amount. The count value CH increases as the motion amount increases, and the count value CL increases as the motion amount decreases. Specifically, a case where the count value CH is equal to or larger then the threshold value TCH corresponds to a case where the motion amount is equal to or larger than the third motion amount, and a case where the count value CL is equal to or larger then the threshold value TCL corresponds to a case where the motion amount is equal to or smaller than the fourth motion amount.

3. First Modification

Figure 12:
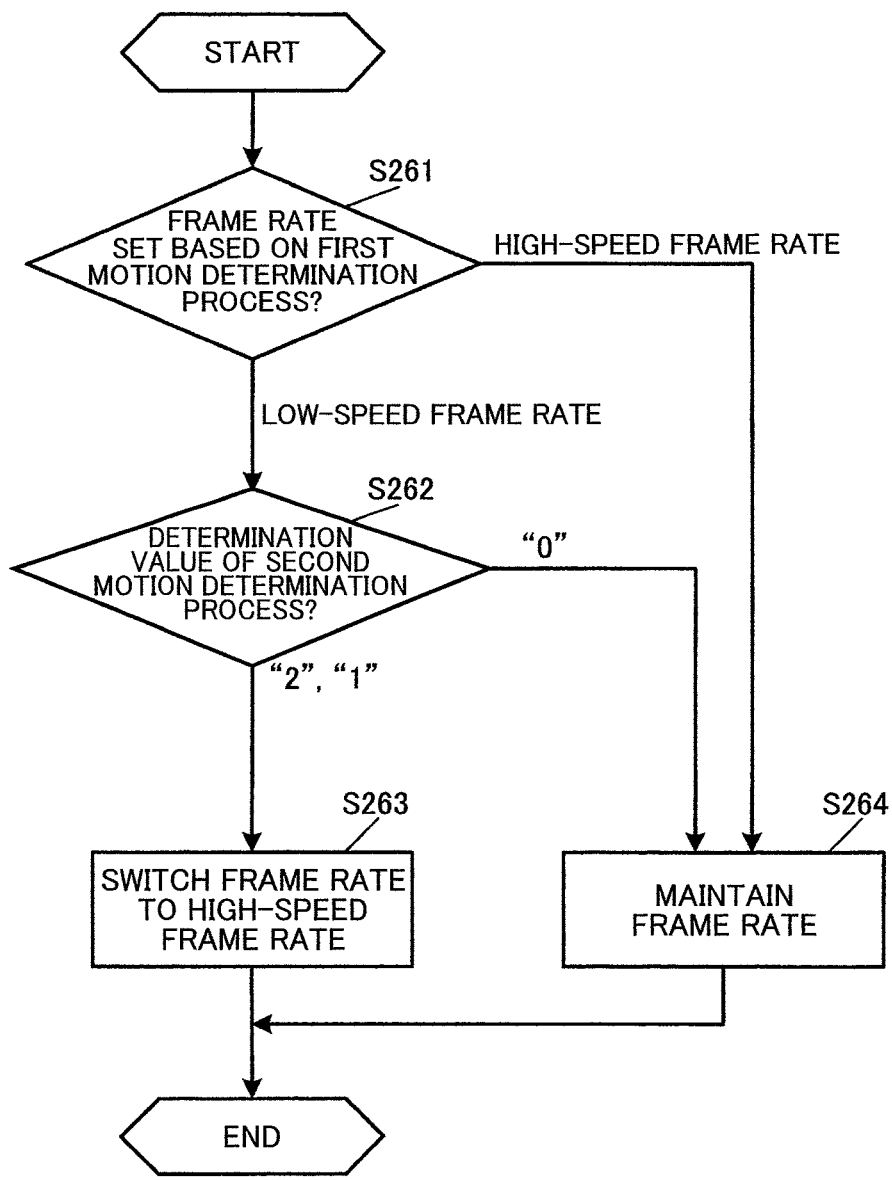
FIG. 12 is a flowchart illustrating a frame rate switch process based on a second motion determination process (first modification).

Several modifications of the embodiments of the invention are described below. FIG. 12 is a flowchart according to a first modification. In the first modification, the frame rate is switched based on the second motion determination process only when the frame rate has been switched to the low-speed frame rate as a result of the first motion determination process.

Specifically, the control process is performed as described below when the frame rate has been set to the low-speed frame rate as a result of the first motion determination process (step S261). The switch determination section 301 determines that the frame rate that has been set as a result of the first motion determination process is not appropriate when the determination value is "2" or "1" (step S262), and switches the frame rate to the high-speed frame rate (step S263). The switch determination section 301 determines that the frame rate that has been set as a result of the first motion determination process is appropriate when the determination value is "0" (step S262), and maintains the low-speed frame rate (step S264).

When the frame rate has been set to the high-speed frame rate as a result of the first motion determination process (step S261), the switch determination section 301 maintains the high-speed frame rate regardless of the determination value (step S264).

According to the first modification, the processing section 120 performs a second determination process that determines whether or not to return the frame rate to the high-speed frame rate based on the second motion determination result (step S262) when the frame rate has been switched from the high-speed frame rate to the low-speed frame rate based on the first motion determination result (S261 illustrated in FIG. 12). The processing section 120 maintains the high-speed frame rate without performing the second determination process (step S264) when the frame rate has been switched from the low-speed frame rate to the high-speed frame rate based on the first motion determination result (S261).

Since the capsule endoscope 100 performs the first motion determination process in a simplified manner, the frame rate may be switched to the low-speed frame rate although the motion speed is high, and a situation in which part of the object is not captured may occur. According to the first modification, it is possible to return the frame rate to the high-speed frame rate through the accurate second motion determination process performed by the external device 200. Therefore, it is possible to reduce or suppress a situation in which part of the object is not captured. When the capsule endoscope 100 has switched the frame rate to the low-speed frame rate, it is unlikely that a situation in which part of the object is not captured occurs even if the determination is incorrect. Therefore, it is safe from the viewpoint of suppressing the occurrence of an incorrect diagnosis even if the determination is not corrected by the external device 200.

4. Second Modification

Figure 13:
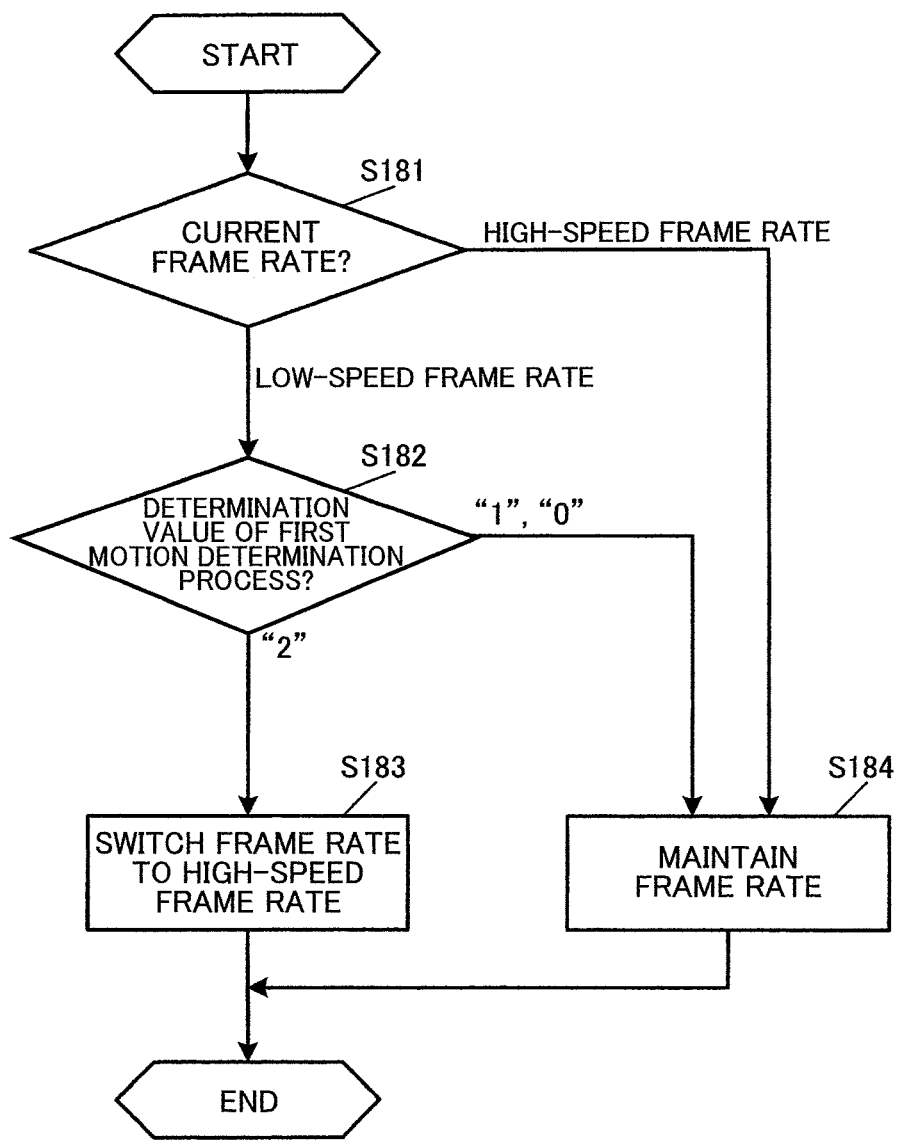
FIG. 13 is a flowchart illustrating a frame rate switch process based on a first motion determination process (second modification).
Figure 14:
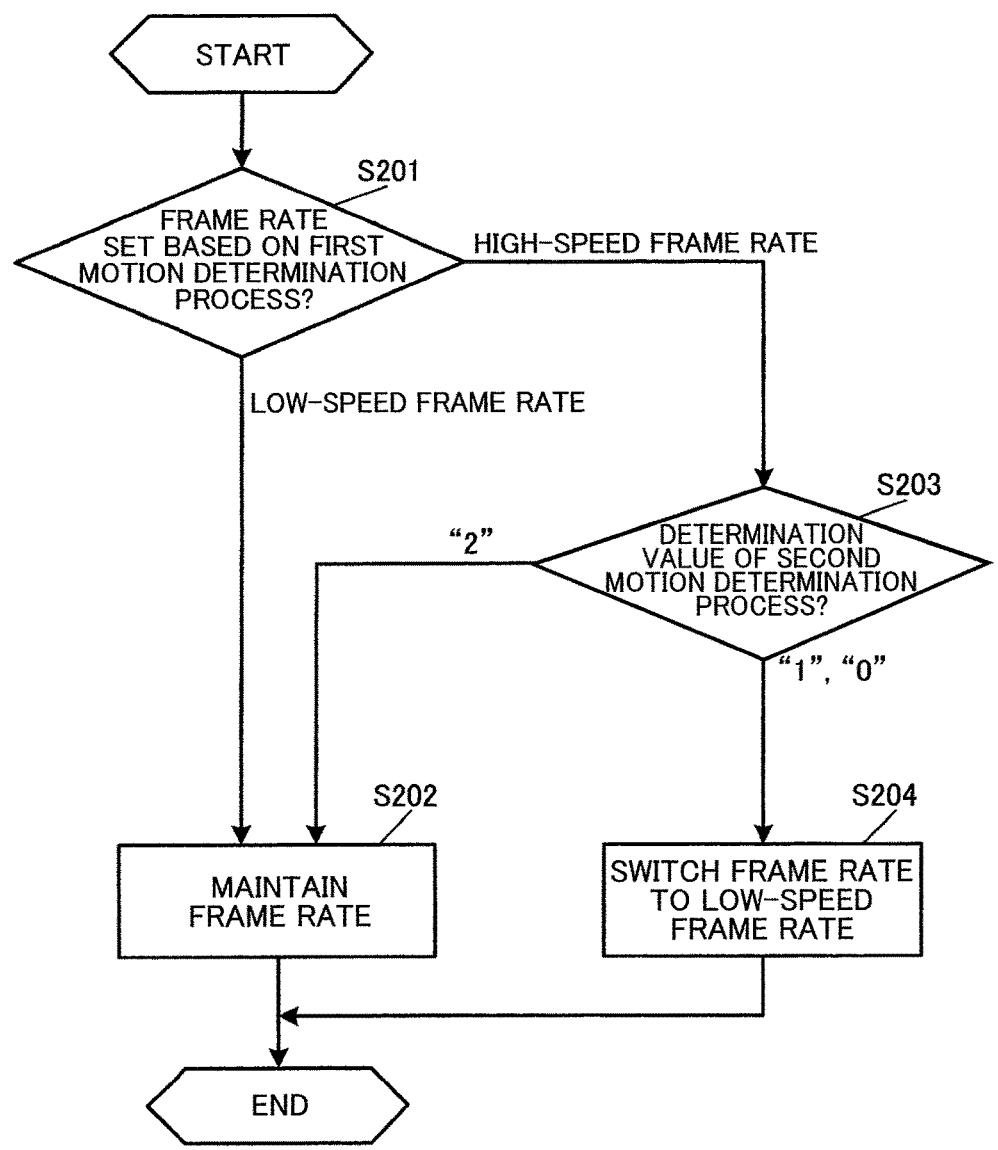
FIG. 14 is a flowchart illustrating a frame rate switch process based on a second motion determination process (second modification).

FIGS. 13 and 14 are flowcharts according to a second modification. In the second modification, the frame rate is switched from the low-speed frame rate to the high-speed frame rate based on the result of the first motion determination process, and is switched from the high-speed frame rate to the low-speed frame rate based on the result of the second motion determination process.

FIG. 13 is a flowchart illustrating the frame rate switch process based on the first motion determination process. The control process is performed as described below when the current frame rate is the low-speed frame rate (step S181). When the determination value is "2" (step S182), the switch determination section 301 switches the frame rate to the high-speed frame rate (step S183). When the determination value is "1" or "0" (step S182), the switch determination section 301 maintains the low-speed frame rate (step S184).

The control process is performed as described below when the current frame rate is the high-speed frame rate (step S181). The switch determination section 301 maintains the high-speed frame rate regardless of the determination value (step S184). Specifically, the switch determination section 301 does not switch the frame rate to the low-speed frame rate.

FIG. 14 is a flowchart illustrating the frame rate switch process based on the second motion determination process. The control process is performed as described below when the frame rate has been set to the low-speed frame rate as a result of the first motion determination process (step S201). The switch determination section 301 maintains the low-speed frame rate regardless of the determination value (step S202). Specifically, the switch determination section 301 does not switch the frame rate to the high-speed frame rate.

The control process is performed as described below when the frame rate has been set to the high-speed frame rate as a result of the first motion determination process (step S201). The switch determination section 301 switches the frame rate to the low-speed frame rate (step S204) when the determination value is "1" or "0" (step S203). The switch determination section 301 maintains the high-speed frame rate (step S202) when the determination value is "2" (step S203).

Note that the frame rate may be switched from the low-speed frame rate to the high-speed frame rate based on the result of the first motion determination process, and may be switched from the high-speed frame rate to the low-speed frame rate, or switched from the low-speed frame rate to the high-speed frame rate, based on the result of the second motion determination process.

According to the second modification, the processing section 120 maintains the frame rate at the high-speed frame rate regardless of the first motion determination result (step S184) in a state in which the frame rate is set to the high-speed frame rate (S181 illustrated in FIG. 13). The processing section 120 switches the frame rate to the high-speed frame rate that is higher than the low-speed frame rate (step S183) when the first motion determination process has determined that the motion amount of the object captured with the captured images is larger than the first motion amount (step S182, determination value: "2") in a state in which the frame rate is set to the low-speed frame rate (step S181).

According to this configuration, the frame rate is not switched from the high-speed frame rate to the low-speed frame rate as a result of the first motion determination process that is performed by the capsule endoscope 100. This makes it possible to prevent a situation in which the frame rate is switched to the low-speed frame rate as a result of the first motion determination process that is performed in a simplified manner although the motion speed is high, and reduce or suppress a situation in which part of the object is not captured.

5. Third Modification

Figure 15:
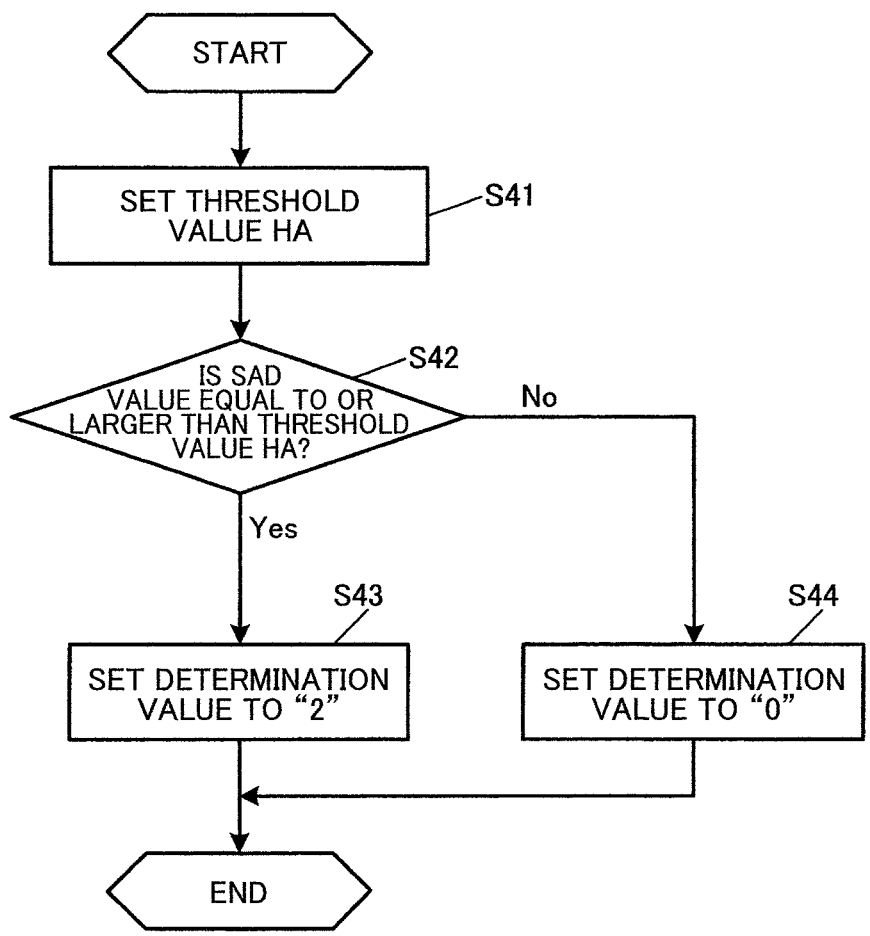
FIG. 15 is a flowchart illustrating a first motion determination process (third modification).

FIG. 15 is a flowchart according to a third modification. The embodiments of the invention have been described above taking an example in which the frame rate is switched in a relative manner. In the third modification, the high-speed frame rate or the low-speed frame rate is selected in an absolute manner.

Specifically, the first motion determination section 122 reads the first threshold value HA from the storage section 150 (step S41). The first motion determination section 122 determines whether or not the SAD value is equal to or larger than the threshold value HA (step S42). When the SAD value is equal to or larger than the threshold value HA, the first motion determination section 122 sets the determination value of the first motion determination process to "2" (step S43). When the SAD value is smaller than the threshold value HA, the first motion determination section 122 sets the determination value to "0" (step S44).

The frame rate switch control process is performed as described below. When using the frame rate switch control process described above with reference to FIG. 10, the current frame rate is maintained regardless of whether the current frame rate is the high-speed frame rate or the low-speed frame rate when the determination value is "1". When using the second modification, the frame rate is switched to the high-speed frame rate (or maintained) when the determination value is "2", and is switched to the low-speed frame rate (or maintained) when the determination value is "0".

Note that the determination value "2" or "0" may also be output during the second motion determination process. In this case, the flowchart illustrated in FIG. 7 is changed so that the threshold value HB is read in the step S81, the steps S84 and S85 are omitted, the count threshold value TCH is read in the step S87, the steps S90 and S92 are omitted, and the step S91 is performed when it has been determined in the step S88 that the count value CH is smaller than the count threshold value TCH.

6. Fourth Modification

Figure 16:
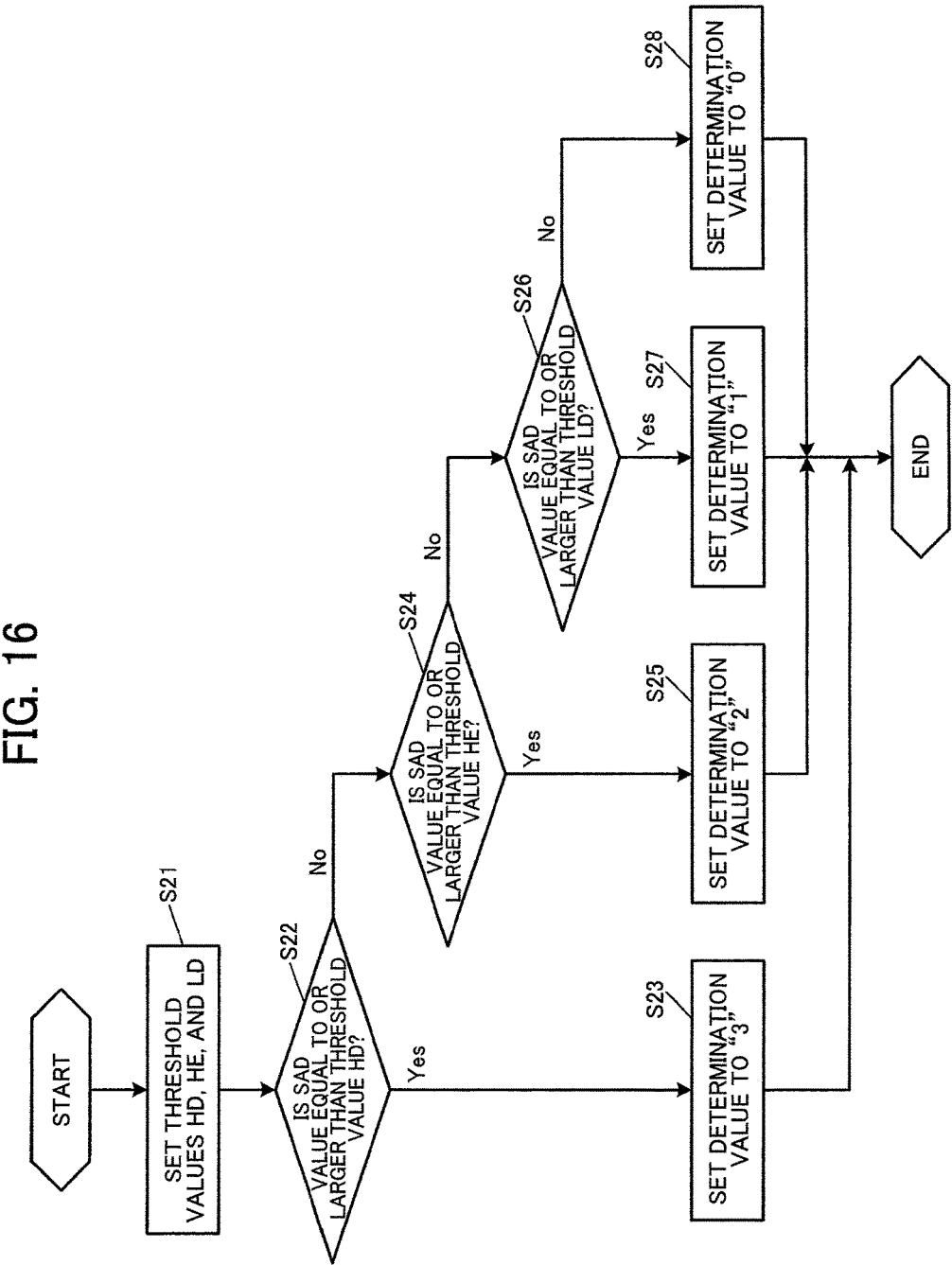
FIG. 16 is a flowchart illustrating a first motion determination process (fourth modification).
Figure 17:
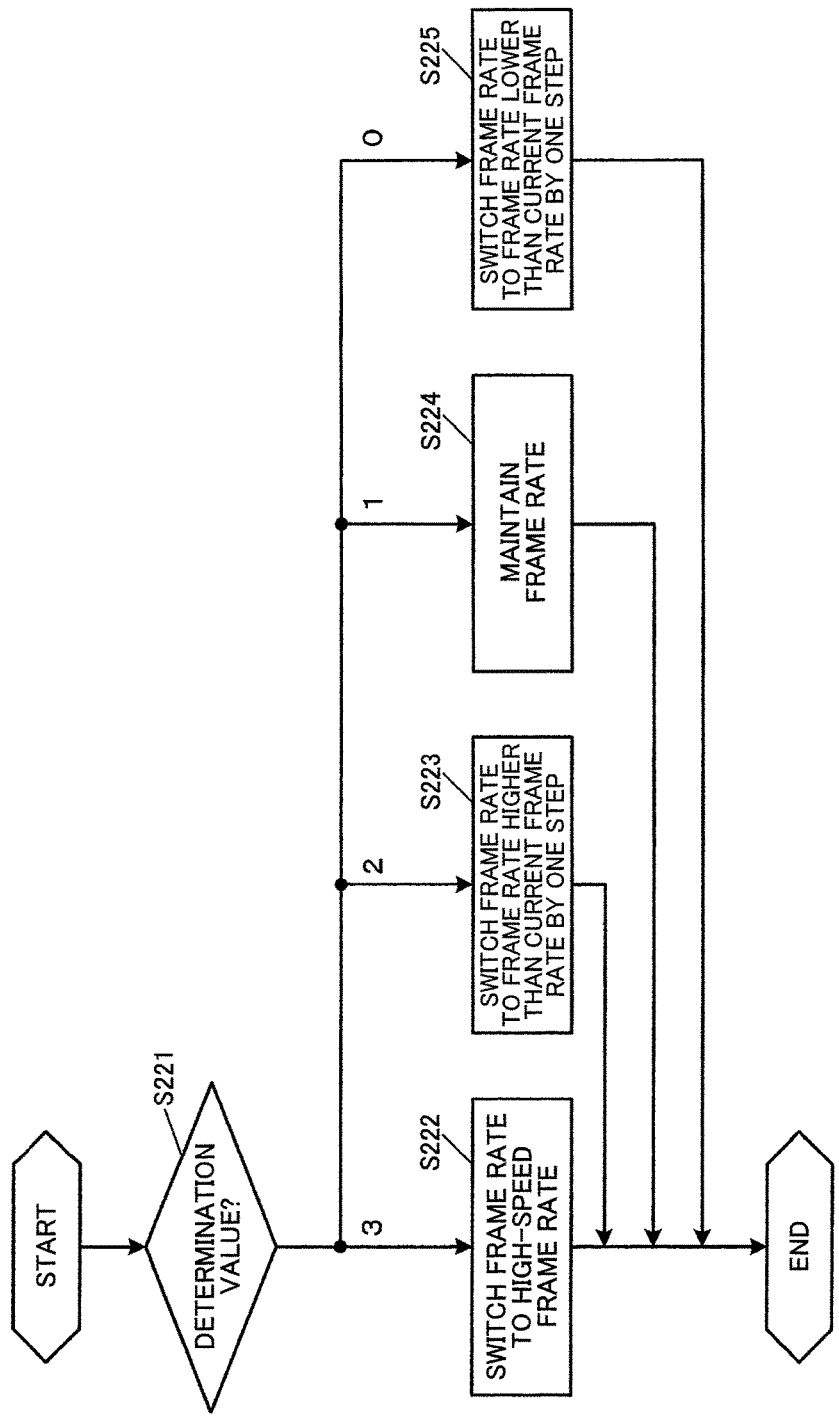
FIG. 17 is a flowchart illustrating a frame rate switch process based on a first motion determination process (fourth modification).

FIGS. 16 and 17 are flowcharts according to a fourth modification. In the fourth modification, the frame rate is switched in n stages (where n is a natural number equal to or larger than 3). An example in which the frame rate is switched to a high-speed frame rate, a medium-speed frame rate, and a low-speed frame rate is described below.

FIG. 16 is a flowchart illustrating the first motion determination process. The first motion determination section 122 reads a first SAD threshold value HD, a second SAD threshold value HE, and a third SAD threshold value LD (HD>HE>LD) from the storage section 150 (step S21).

The first motion determination section 122 determines whether or not the SAD value is equal to or larger than the threshold value HD (step S22). When the SAD value is equal to or larger than the threshold value HD, the first motion determination section 122 sets the determination value of the first motion determination process to "3" (step S23). When the SAD value is smaller than the threshold value HD, the first motion determination section 122 determines whether or not the SAD value is equal to or larger than the threshold value HE (step S24). When the SAD value is equal to or larger than the threshold value HE, the first motion determination section 122 sets the determination value to "2" (step S25). When the SAD value is smaller than the threshold value HE, the first motion determination section 122 determines whether or not the SAD value is equal to or larger than the threshold value LD (step S26). When the SAD value is equal to or larger than the threshold value LD, the first motion determination section 122 sets the determination value to "1" (step S27). When the SAD value is smaller than the threshold value LD, the first motion determination section 122 sets the determination value to "0" (step S28).

FIG. 17 is a flowchart illustrating the frame rate switch process based on the first motion determination process. When the determination value of the first motion determination process is "3" (step S221), the frame rate control section 124 switches the frame rate to the high-speed frame rate (step S222). When the determination value is "2" (step S221), the frame rate control section 124 switches the frame rate to a frame rate that is higher than the current frame rate by one step (step S223). For example, the frame rate control section 124 switches the frame rate from the low-speed frame rate to the medium-speed frame rate. Note that the high-speed frame rate is maintained in the steps S222 and S223 when the current frame rate is the high-speed frame rate.

When the determination value is "1" (step S221), the frame rate control section 124 maintains the current frame rate (step S224). When the determination value is "1" (step S221), the frame rate control section 124 switches the frame rate to a frame rate that is lower than the current frame rate by one step (step S225). For example, the frame rate control section 124 switches the frame rate from the high-speed frame rate to the medium-speed frame rate. Note that the low-speed frame rate is maintained in the step S225 when the current frame rate is the low-speed frame rate.

The second motion determination process is performed as described below, for example. A third count threshold value TCH' is additionally provided, and the count threshold values TCH, TCH', and TCL (T C H>T C H' ,s,b,k) are read in the step S87 (see FIG. 7). When the count value CH is equal to or larger than the threshold value TCH in the step S88, the determination value is set to "3" in the step S89. When the count value CH is smaller than the threshold value TCH, whether or not the count value CH is equal to or larger than the threshold value TCH' is determined. When the count value CH is equal to or larger than the threshold value TCH', the determination value is set to "2". When the count value CH is smaller than the threshold value TCH', the step S90 is performed.

The frame rate control process using the determination value of the second motion determination process is performed in the same manner as described with reference to FIG. 17 (flowchart). The frame rate is switched when a frame rate that differs from the frame rate set based on the first motion determination process has been selected. The current frame rate is maintained when the same frame rate as the frame rate set based on the first motion determination process has been selected.

According to the fourth modification, the processing section 120 compares the motion amount (SAD value) with first to third motion amounts (threshold values HD, HE, and LD) to determine whether to switch the frame rate to the highest frame rate among first to nth frame rates (high-speed frame rate, medium-speed frame rate, and low-speed frame rate) (step S222), switch the frame rate to a frame rate that is higher than the current frame rate by one step (step S223), maintain the current frame rate (step S224), or switch the frame rate to a frame rate that is lower than the current frame rate by one step (step S225).

In this case, the processing section 120 calculates the motion amount of the object from the captured images that were captured at the current frame rate (i.e., the frame rate that is currently set).

For example, when the frame rate is set to 12, 8, or 4 fps, the processing section 120 calculates the motion amount of the object from the captured images that were captured at a frame rate of 12, 8, or 4 fps. Specifically, the processing section 120 calculates the motion amount from the captured images that are contiguous to each other on a time-series basis (i.e., the captured images selected without a skip) regardless of the frame rate.

The storage section 150 stores the first to nth frame rates (high-speed frame rate, medium-speed frame rate, and low-speed frame rate), the first to third motion amounts (threshold values HD, HE, and LD), and the relationship between the switch control process with respect to the first to nth frame rates and the first to third motion amounts (e.g., the threshold values HD, HE, and LD, the determination value determined using the threshold values HD, HE, and LD, and the relationship between the determination value and the frame rate control process).

It is desirable to necessarily capture the digestive tract at constant intervals in order to prevent a situation in which part of the object is not captured. When the digestive tract is captured at constant intervals, the inter-frame motion amount is apparently constant. Specifically, when the frame rate is appropriately controlled corresponding to the actual motion speed of the capsule endoscope 100, and the digestive tract is captured at constant intervals, the inter-frame motion amount is apparently constant regardless of the frame rate. When the motion speed has changed in such a state, the inter-frame motion amount increases or decreases. Therefore, it is possible to switch the frame rate to an appropriate frame rate by detecting a change in inter-frame motion amount. According to the fourth modification, since the motion determination process is performed using the frame rate that was used when the captured images were captured, it is possible to perform a relative motion detection process. Specifically, when the motion speed has changed with respect to the frame rate as described above, it is possible to detect the direction in which the motion speed has changed, and cause the frame rate to follow the detected direction. This makes it possible to capture the digestive tract at appropriate intervals. Since the necessary parameters are stored in the storage section 150 in advance, it is possible to implement the motion determination process using the capsule endoscope 100, and implement a frame rate control process without a time lag.

Although the fourth modification illustrates the case where n is equal to or larger than 3, the first detailed configuration example illustrates the case where n is 2. Therefore, n may be set to be equal to or larger than 2.

According to the fourth modification, the communication section 130 adaptively adjusts the transmission rate of the captured images corresponding to the frame rate, and transmits the captured images that were captured at the current frame rate to the external device 200.

According to this configuration, the external device 200 can perform the second motion determination process using the captured images that were captured under the same conditions as those of the captured images used for the first motion determination process performed by the capsule endoscope 100. This makes it possible to accurately determine the appropriateness of the result of the first motion determination process using the second motion determination process.

7. Fifth Modification

Figure 18:
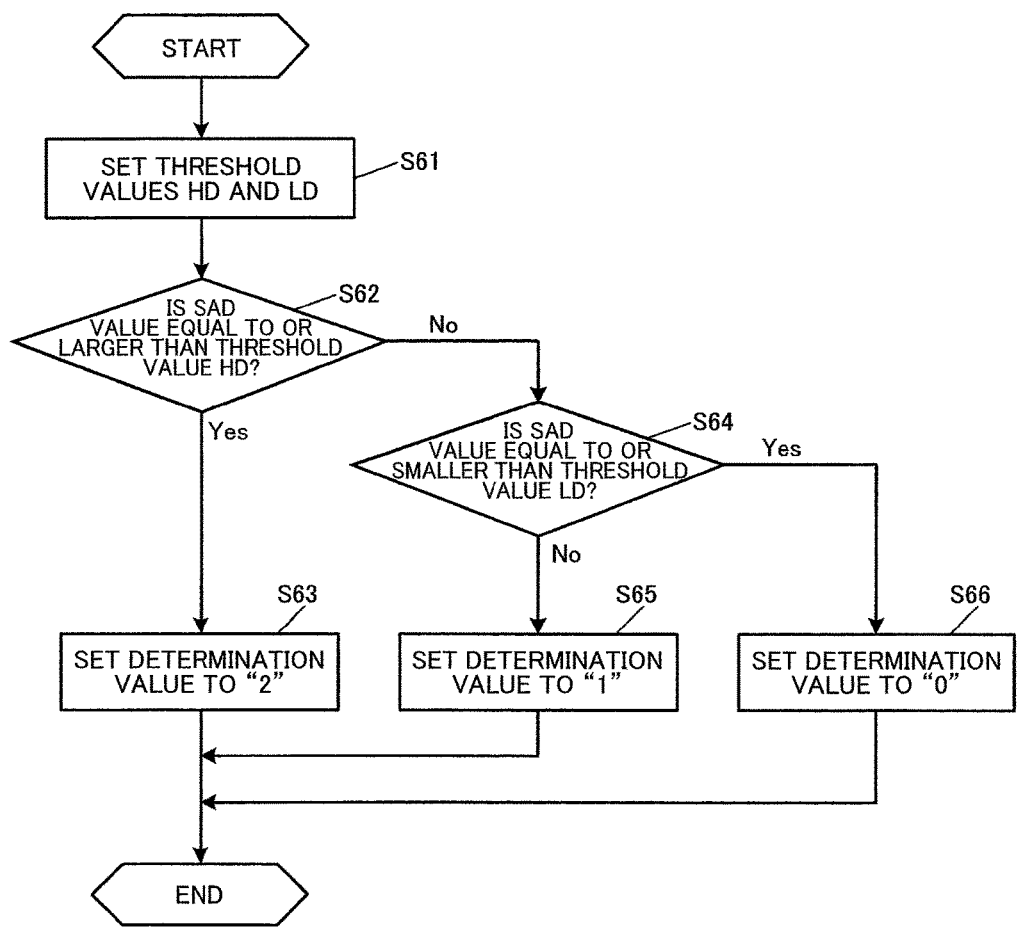
FIG. 18 is a flowchart illustrating a first motion determination process (fifth modification).
Figure 19:
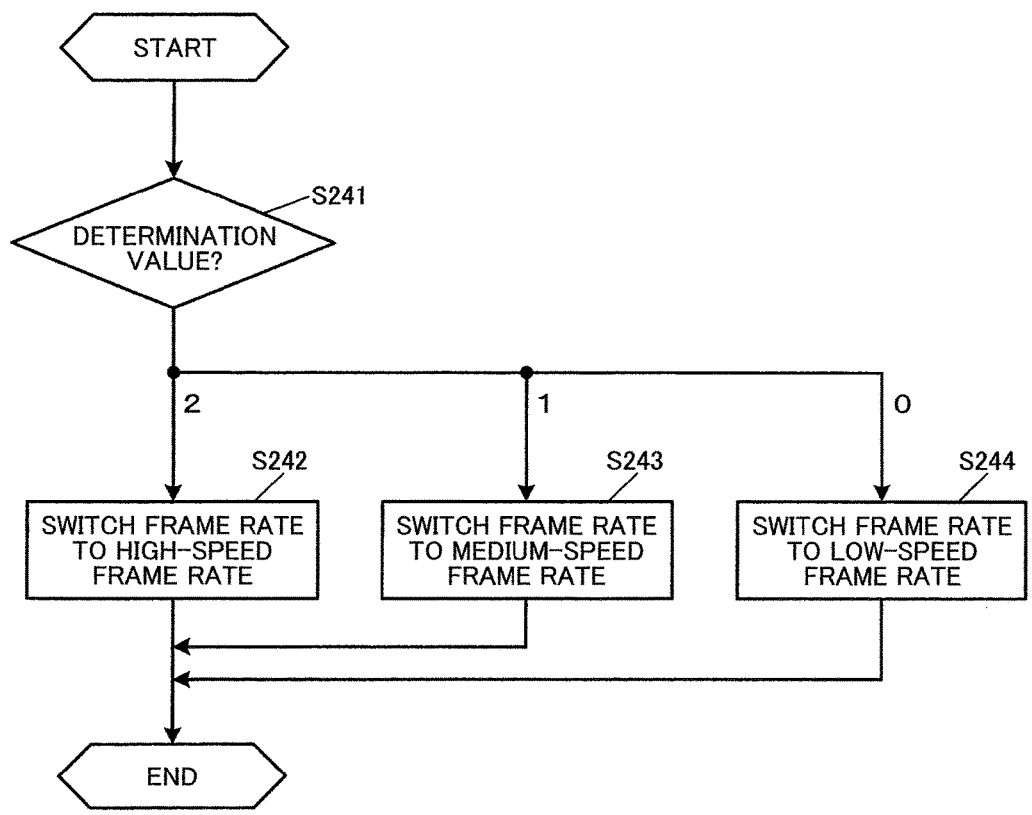
FIG. 19 is a flowchart illustrating a frame rate switch process based on a first motion determination process (fifth modification).

FIGS. 18 and 19 are flowcharts according to a fifth modification. In the fourth modification, the frame rate is switched in a relative manner. In the fifth modification, the frame rate is selected in an absolute manner.

FIG. 18 is a flowchart illustrating the first motion determination process. The first motion determination section 122 reads the first SAD threshold value HD and the second SAD threshold value LD (HD>LD) from the storage section 150 (step S61).

The first motion determination section 122 determines whether or not the SAD value is equal to or larger than the threshold value HD (step S62). When the SAD value is equal to or larger than the threshold value HD, the first motion determination section 122 sets the determination value of the first motion determination process to "2" (step S63). When the SAD value is smaller than the threshold value HD, the first motion determination section 122 determines whether or not the SAD value is equal to or smaller than the threshold value LD (step S64). When the SAD value is equal to or smaller than the threshold value LD, the first motion determination section 122 sets the determination value to "0" (step S66). When the SAD value is larger than the threshold value LD, the first motion determination section 122 sets the determination value to "1" (step S65).

FIG. 19 is a flowchart illustrating the frame rate switch process based on the first motion determination process. When the determination value of the first motion determination process is "2" (step S241), the frame rate control section 124 switches the frame rate to the high-speed frame rate (step S242). When the current frame rate is the high-speed frame rate, the frame rate control section 124 maintains the high-speed frame rate. When the determination value is "1" (step S241), the frame rate control section 124 switches the frame rate to the medium-speed frame rate (step S243). When the current frame rate is the medium-speed frame rate, the frame rate control section 124 maintains the medium-speed frame rate. When the determination value is "0" (step S241), the frame rate control section 124 switches the frame rate to the low-speed frame rate (step S244). When the current frame rate is the low-speed frame rate, the frame rate control section 124 maintains the low-speed frame rate.

Note that the second motion determination process is performed in the same manner as described above with reference to FIG. 7 (flowchart), for example. The frame rate control process using the determination value of the second motion determination process is performed in the same manner as described with reference to FIG. 19 (flowchart). The frame rate is switched when a frame rate that differs from the frame rate set based on the first motion determination process has been selected. The current frame rate is maintained when the same frame rate as the frame rate set based on the first motion determination process has been selected.

According to the fifth modification, the processing section 120 compares the motion amount (SAD value) with the first to (n−1)th motion amounts (threshold values HD and LD) to determine a frame rate among the first to nth frame rates (high-speed frame rate, medium-speed frame rate, and low-speed frame rate) to which the frame rate is switched.

In this case, the processing section 120 extracts captured images at an identical frame rate from the captured images captured at the frame rate to calculate the motion amount of the object regardless of whether the frame rate is set to which frame rate among the first to nth frame rates.

For example, when the frame rate is set to 12, 8, or 4 fps, the processing section 120 extracts the captured images at a frame rate of 4 fps regardless of whether the frame rate is set to 12, 8, or 4 fps, and calculates the motion amount from the captured images extracted at a frame rate of 4 fps. Specifically, when the frame rate is set to 12 fps, the processing section 120 selects every third captured image (i.e., skips two captured images). When the current frame rate is set to 8 fps, the processing section 120 selects every second captured image (i.e., skips one captured image). When the current frame rate is set to 4 fps, the processing section 120 selects every captured image (i.e., selects the captured images that are contiguous to each other on a time-series basis).

The storage section 150 stores the first to nth frame rates (high-speed frame rate, medium-speed frame rate, and low-speed frame rate), the first to (n−1)th motion amounts (threshold values HD and LD), and the relationship between the first to nth frame rates and the first to (n−1)th motion amounts (e.g., the threshold values HD and LD, the determination value determined using the threshold values HD and LD, and the relationship between the determination value and the frame rate).

The inter-frame motion amount apparently decreases as the frame rate increases even when the motion speed is identical. Therefore, the motion determination process is affected by the frame rate. According to the fifth modification, it is possible to calculate the absolute motion amount regardless of the current frame rate, and perform the motion determination process. This makes it possible to implement a stable frame rate switch control process that is not affected by the frame rate. Since the necessary parameters are stored in the storage section 150 in advance, it is possible to implement the motion determination process using the capsule endoscope 100, and implement a frame rate control process without a time lag. Since the frame rate of the images used for the motion determination process is low, it is possible to reduce power consumption.

Although the fifth modification illustrates the case where n is equal to or larger than 3, the third modification illustrates the case where n is 2. Therefore, n may be set to be equal to or larger than 2.

According to the fifth modification, the communication section 130 sets the transmission rate of the captured images to a given transmission rate, and transmits the captured images extracted at the same frame rate to the external device 200.

According to this configuration, the external device 200 can perform the second motion determination process using the captured images that were captured under the same conditions as those of the captured images used for the first motion determination process performed by the capsule endoscope 100. This makes it possible to accurately determine the appropriateness of the result of the first motion determination process using the second motion determination process. Since the frame rate of the captured images to be transmitted is low, it is possible to reduce the power consumption of the capsule endoscope 100.

Although the fourth modification has been described above taking an example in which the motion determination process is performed using the captured images that were captured at the current frame rate, and the fifth modification has been described above taking an example in which the captured images are extracted at the same frame rate regardless of the current frame rate, and the motion determination process is performed using the extracted captured images, these methods may be selectively used in an interchangeable manner.

This makes it possible to select an appropriate frame rate control method corresponding to the patient, the details of the diagnosis, and the like.

8. Second Detailed Configuration

Figure 20:
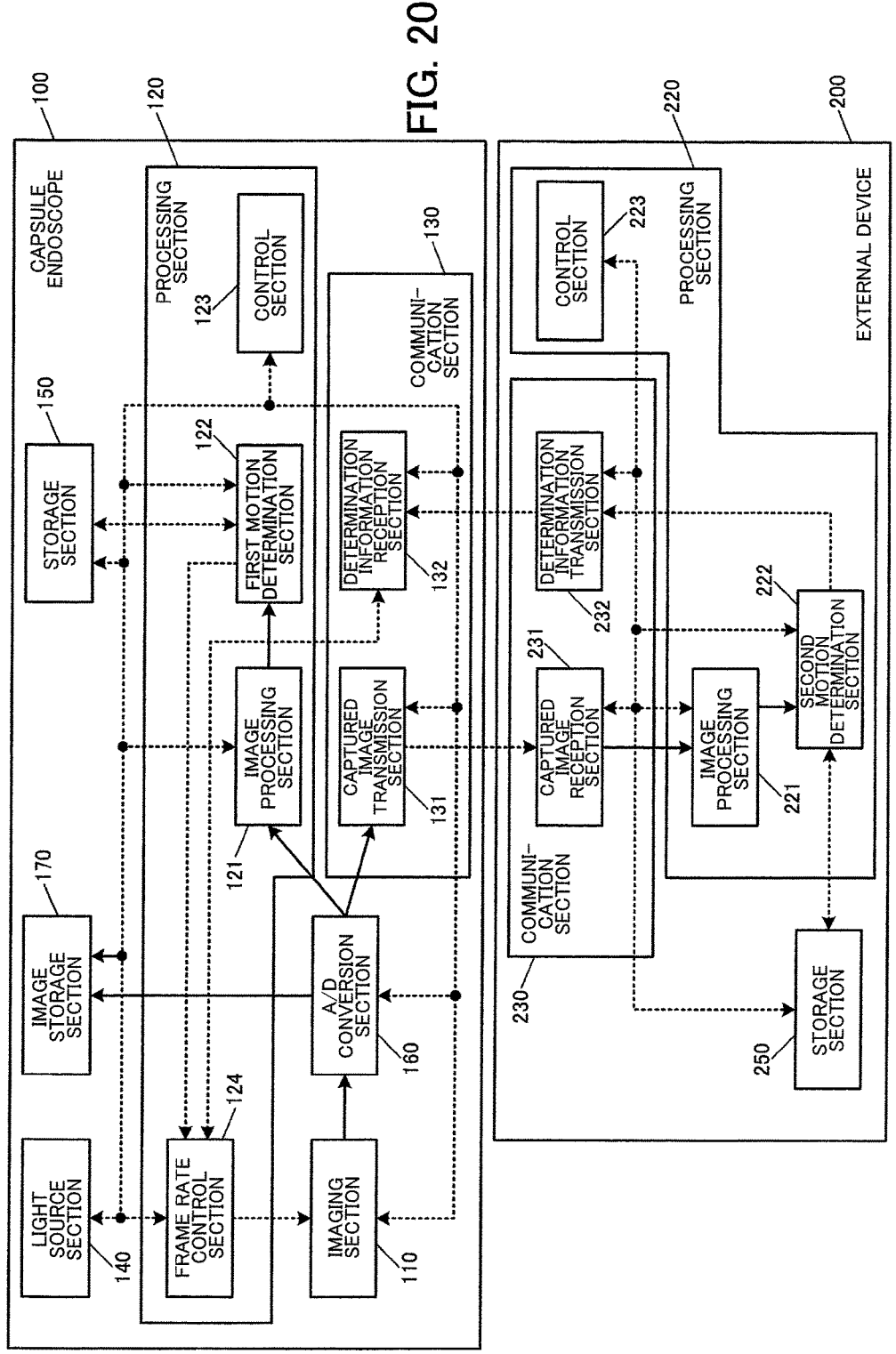
FIG. 20 illustrates a second detailed configuration example of an endoscope system.

FIG. 20 illustrates a second detailed configuration example of the endoscope system. The endoscope system includes a capsule endoscope 100 (capsule main body) and an external device 200 (extracorporeal device). Note that the same elements as those described above in connection with the first detailed configuration example are indicated by the same reference signs (symbols), and description thereof is appropriately omitted. The differences from the first detailed configuration example are described below.

The capsule endoscope 100 additionally includes an image storage section 170, and the image storage section 270 is omitted from the external device 200. The A/D conversion section 160 is connected to the image storage section 270. The image storage section 270 is bidirectionally connected to the control section 123.

The captured image captured by the imaging section 110 is A/D-converted by the A/D conversion section 160, and transmitted to the image storage section 170, the image processing section 121, and the captured image transmission section 131. The image storage section 170 stores the captured image transmitted from the A/D conversion section 160. Specifically, the captured image is stored in the capsule endoscope 100 instead of the external device 200.

The captured image transmission section 131 transmits the captured images to the external device 200 under control of the control section 123 when the frame rate control section 124 has switched the frame rate as a result of the first motion determination process. In this case, the captured image transmission section 131 transmits the captured images among the time-series captured images that were used for the first motion determination process.

Note that the captured image transmission section 131 may transmit the captured images used for the first motion determination process to the external device 200 under control of the control section 123 when the frame rate has been switched from the high-speed frame rate to the low-speed frame rate as a result of the first motion determination process. Since a situation in which the entire image is not captured may occur when the frame rate has been erroneously switched to the low-speed frame rate, it is possible to reduce or suppress a situation in which an incorrect diagnosis is made by transmitting the captured images used for the first motion determination process to the external device 200. It is possible to reduce power consumption by transmitting the captured images used for the first motion determination process to the external device 200 only when the frame rate has been switched to the low-speed frame rate.

The captured image reception section 231 included in the external device 200 receives the captured images transmitted from the capsule endoscope 100. The second motion determination section 222 performs the second motion determination process using the captured images used for the first motion determination process, and the determination information transmission section 232 transmits the result of the second motion determination process to the capsule endoscope 100.

According to the second detailed configuration example, the communication section 130 transmits the captured images used to obtain the first motion determination result to the external device 200 when it has been determined by the first determination process to switch the frame rate. The processing section 120 performs the second determination process based on the second motion determination result obtained based on the captured images used to obtain the first motion determination result.

According to this configuration, the second motion determination process is performed based on the captured images used for the first motion determination process each time the frame rate is switched based on the first motion determination result. Since the second motion determination process is used to determine the appropriateness of the result of the first motion determination process, it is possible to perform the second motion determination process using only the captured images necessary (appropriate) for determining the appropriateness of the result of the first motion determination process by utilizing the captured images used for the first motion determination process. Since the second motion determination process is not performed using unnecessary captured images, it is possible to reduce power consumption.

The embodiments to which the invention is applied and the modifications thereof have been described above. Note that the invention is not limited to the above embodiments and the modifications thereof. Various modifications and variations may be made without departing from the scope of the invention. A plurality of elements described above in connection with the embodiments and the modifications thereof may be appropriately combined to implement various configurations. For example, some of the elements described above in connection with the embodiments and the modifications thereof may be omitted. Some of the elements described above in connection with different embodiments or modifications thereof may be appropriately combined. Specifically, various modifications and applications are possible without materially departing from the novel teachings and advantages of the invention. Any term cited with a different term having a broader meaning or the same meaning at least once in the specification and the drawings can be replaced by the different term in any place in the specification and the drawings.

What is claimed is:

1. A capsule endoscope comprising:
   an imaging device that captures time-series captured images; and
   a processor comprising hardware, the processor being configured to implement processes comprising:
   a process that performs a first motion determination process with respect to the capsule endoscope based on the captured images to calculate a first motion determination result; and
   a communication process that transmits the captured images to an external device that is provided outside the capsule endoscope, and receives a second motion determination result, the second motion determination result being a result of a second motion determination process with respect to the capsule endoscope that was performed by the external device based on the captured images, wherein the processor is configured to implement a process that controls a frame rate of the imaging device based on the first motion determination result and the second motion determination result, wherein the processor is configured to implement a process that performs a first determination process that determines the frame rate based on the first motion determination result, controls the frame rate based on the first determination process, performs a second determination process that determines whether or not the frame rate determined based on the first motion determination result is appropriate based on the second motion determination result, and controls the frame rate by determining the frame rate based on the second motion determination result when the process has determined that the frame rate determined based on the first motion determination result is not appropriate, wherein the processor is configured to implement a process that switches the frame rate to a high-speed frame rate when it has been determined by the first motion determination process that a motion amount of an object captured within the captured images is larger than a first motion amount, and switches the frame rate to a low-speed frame rate that is lower than the high-speed frame rate when it has been determined by the first motion determination process that the motion amount is smaller than a second motion amount that is smaller than the first motion amount, and wherein the processor is configured to implement a process that switches the frame rate to the high-speed frame rate when it has been determined by the second motion determination process that the motion amount is larger than a third motion amount in a state in which the frame rate is set to the low-speed frame rate, and switches the frame rate to the low-speed frame rate when it has been determined by the second motion determination process that the motion amount is smaller than a fourth motion amount that is smaller than the third motion amount in a state in which the frame rate is set to the high-speed frame rate.

2. The capsule endoscope as defined in claim 1, wherein:
the processor is configured to implement the communication process that transmits the captured images that were used to obtain the first motion determination result to the external device when it has been determined by the first determination process to switch the frame rate, and the processor is configured to implement the process that performs the second determination process based on the second motion determination result that was obtained based on the captured images that were used to obtain the first motion determination result.

3. The capsule endoscope as defined in claim 1, further comprising:
a memory that stores first to nth frame rates (where n is a natural number equal to or larger than 2), first to (n−1)th motion amounts, and a relationship between the first to nth frame rates and the first to (n−1)th motion amounts, wherein the processor is configured to implement a process that extracts captured images at an identical frame rate from the captured images that were captured at the frame rate to calculate a motion amount of an object regardless of whether the frame rate to which the frame rate is set among the first to nth frame rates, and compares the motion amount with the first to (n−1)th motion amounts to determine a frame rate among the first to nth frame rates to which the frame rate is switched.

4. The capsule endoscope as defined in claim 3, wherein the processor is configured to implement the communication process that sets a transmission rate of the captured images to a given transmission rate, and transmits the captured images extracted at the identical frame rate to the external device.

5. The capsule endoscope as defined in claim 1, further comprising:
a memory that stores first to nth frame rates (where n is a natural number equal to or larger than 2), first to third motion amounts, and a relationship between a switch control process with respect to the first to nth frame rates and the first to third motion amounts, wherein the processor is configured to implement a process that calculates a motion amount of an object from the captured images that were captured at a frame rate, and compares the motion amount with the first to third motion amounts to determine whether to switch the frame rate to a highest frame rate among the first to nth frame rates, switch the frame rate to a frame rate that is higher than a current frame rate by one step, maintain the current frame rate, or switch the frame rate to a frame rate that is lower than the current frame rate by one step.

6. The capsule endoscope as defined in claim 5, wherein the processor is configured to implement the communication process that adaptively adjusts a transmission rate of the captured images corresponding to the frame rate, and transmits the captured images that were captured at the frame rate to the external device.

7. The capsule endoscope as defined in claim 1, wherein:
the external device performs the second motion determination process that requires a second processing load, and the processor is configured to implement the process that performs the first motion determination process that requires a first processing load that is lower than the second processing load.

8. An endoscope system comprising:
the capsule endoscope according to claim 1; and
the external device, the external device comprising:
a second processor comprising hardware, the second processor being configured to implement processes comprising:
a second process that performs a second motion determination process with respect to the capsule endoscope based on the captured images, and outputs the second motion determination result; and
a second communication process that transmits the second motion determination result to the capsule endoscope.

9. A method for operating the capsule endoscope according to claim 1, the method comprising:
capturing the time-series captured images;
performing the first motion determination process with respect to the capsule endoscope based on the captured images to calculate the first motion determination result;
transmitting the captured images to the external device that is provided outside the capsule endoscope;
receiving the second motion determination result from the external device; and controlling the frame rate used when capturing the captured images based on the first motion determination result and the second motion determination result.

10. A capsule endoscope comprising:
an imaging device that captures time-series captured images; and
a processor comprising hardware, the processor being configured to implement processes comprising:
a process that performs a first motion determination process with respect to the capsule endoscope based on the captured images to calculate a first motion determination result; and
a communication process that transmits the captured images to an external device that is provided outside the capsule endoscope, and receives a second motion determination result, the second motion determination result being a result of a second motion determination process with respect to the capsule endoscope that was performed by the external device based on the captured images,
wherein the processor is configured to implement a process that controls a frame rate of the imaging device based on the first motion determination result and the second motion determination result,
wherein the processor is configured to implement a process that performs a first determination process that determines the frame rate based on the first motion determination result, controls the frame rate based on the first determination process, performs a second determination process that determines whether or not the frame rate determined based on the first motion determination result is appropriate based on the second motion determination result, and controls the frame rate by determining the frame rate based on the second motion determination result when the process has determined that the frame rate determined based on the first motion determination result is not appropriate,
wherein the processor is configured to implement a process that switches the frame rate to a high-speed frame rate when it has been determined by the first motion determination process that a motion amount of an object captured within the captured images is larger than a first motion amount, and switches the frame rate to a low-speed frame rate that is lower than the high-speed frame rate when it has been determined by the first motion determination process that the motion amount is smaller than a second motion amount that is smaller than the first motion amount, and
wherein the processor is configured to implement a process that performs the second determination process that determines whether or not to return the frame rate to the high-speed frame rate based on the second motion determination result when the frame rate has been switched from the high-speed frame rate to the low-speed frame rate based on the first motion determination result, and maintains the high-speed frame rate without performing the second determination process when the frame rate has been switched from the low-speed frame rate to the high-speed frame rate based on the first motion determination result.

11. A capsule endoscope comprising:
an imaging device that captures time-series captured images; and
a processor comprising hardware, the processor being configured to implement processes comprising:
a process that performs a first motion determination process with respect to the capsule endoscope based on the captured images to calculate a first motion determination result; and
a communication process that transmits the captured images to an external device that is provided outside the capsule endoscope, and receives a second motion determination result, the second motion determination result being a result of a second motion determination process with respect to the capsule endoscope that was performed by the external device based on the captured images,
wherein the processor is configured to implement a process that controls a frame rate of the imaging device based on the first motion determination result and the second motion determination result,
wherein the processor is configured to implement a process that performs a first determination process that determines the frame rate based on the first motion determination result, controls the frame rate based on the first determination process, performs a second determination process that determines whether or not the frame rate determined based on the first motion determination result is appropriate based on the second motion determination result, and controls the frame rate by determining the frame rate based on the second motion determination result when the process has determined that the frame rate determined based on the first motion determination result is not appropriate, and
wherein the processor is configured to implement a process that switches the frame rate to a high-speed frame rate that is higher than a low-speed frame rate, when the frame rate has been set to the low-speed frame rate and when it has been determined by the first motion determination process that a motion amount of an object captured within the captured images is larger than a first motion amount, and that maintains the frame rate at the high-speed frame regardless of the first motion determination result when the frame rate has been set to the high-speed frame rate.

12. The capsule endoscope as defined in claim 11, wherein the processor is configured to implement a process that determines whether or not to switch the frame rate to the high-speed frame rate based on the first motion determination result, and determines whether or not to switch the frame rate to the low-speed frame rate based on the second motion determination result.

* * * * *